(12) United States Patent
Gokce et al.

(10) Patent No.: US 8,202,552 B2
(45) Date of Patent: Jun. 19, 2012

(54) INSECTICIDAL COMPOSITIONS AND USES THEREOF

(75) Inventors: Ayhan Gokce, Tokat (TR); Mark E. Whalon, Mason, MI (US); Ibrahim Demirtas, Tokat (TR); Nezhun Goren, Istanbul (TR)

(73) Assignee: Board of Trustees of Michigan State University, East Lansing, MI (US)

( * ) Notice: Subject to any disclaimer, the term of this patent is extended or adjusted under 35 U.S.C. 154(b) by 79 days.

(21) Appl. No.: 12/085,535

(22) PCT Filed: Nov. 28, 2006

(86) PCT No.: PCT/US2006/045538
§ 371 (c)(1),
(2), (4) Date: Jul. 31, 2009

(87) PCT Pub. No.: WO2007/062248
PCT Pub. Date: May 31, 2007

(65) Prior Publication Data
US 2010/0055208 A1    Mar. 4, 2010

(51) Int. Cl.
*A01N 65/00* (2009.01)
(52) U.S. Cl. .................................................. 424/725
(58) Field of Classification Search .................. None
See application file for complete search history.

(56) References Cited

U.S. PATENT DOCUMENTS

| | | | | |
|---|---|---|---|---|
| 3,552,975 | A * | 1/1971 | Worden et al. | 426/538 |
| 3,607,300 | A * | 9/1971 | Mitchell | 426/600 |
| 6,641,827 | B2 | 11/2003 | Yoshida et al. | 424/405 |
| 6,855,348 | B2 | 2/2005 | Ahn et al. | 424/739 |
| 2002/0132021 | A1 | 9/2002 | Raskin et al. | 424/773 |
| 2003/0211788 | A1* | 11/2003 | Murakami et al. | 439/894 |
| 2004/0024026 | A1 | 2/2004 | Morita et al. | 514/341 |
| 2005/0070576 | A1 | 3/2005 | Spooner-Hart et al. | 514/317 |
| 2005/0220914 | A1 | 10/2005 | Probasco et al. | 424/778 |

FOREIGN PATENT DOCUMENTS

WO    WO 02/089587    11/2002 ............... 35/6

OTHER PUBLICATIONS

Anaya et al., "Allelochemical potential of *Callicarpa acuminate*." *J Chem Ecol.* 29: 2761-76 (2003).
Bartelt et al., "Orientation and feeding responses of the pollen beetle, *Meligethes aeneus*, to candytuft, Iberis amara." *J. Chem. Ecol.*, 30: 913-925 (2004).
Bentley et al., "Limonoid model insect antifeedants." *J Agric Food Chem.*, 38: 1400-1403 (1990).
Bomford and Isman, "Desensitization of fifth instar *Spodoptera litura* to azadirachtin and neem." *Entomol Exp Appl*, 81: 301-313 (1996).
Bruno et al., "Neoclerodane diterpenoids from *Teucrium polium* subsp. *polium* and their antifeedant activity." *Biochem. Syst. Ecol.*, 31: 1051-1056 (2003).

Carde and Roelofs, "Attraction of redbanded leafroller moths,*Argyrotaenia velutinana*, to blends of (Z)-and (E)-11-tridecenyl acetates." *J. Chem. Ecol.*, 3: 143-146 (1977).
Centisoy et al., "Investigations on repellant and insecticidal effects of *Xanthium strumarium* L. on Colorado Potato Beetle leptinotrasa decemlineata: Say (Col: Chrysomelidae." *Turk J of Agric Forest*, 22: 543-552 (1998).
Chapman, "Bionomics of the apple-feeding tortricidae." *Annu. Rev. Entomol.*, 18: 73-96 (1973).
Chapman et al., "Bionomics of *Choristoneura rosaceana*." *Ann. Entomol. Soc. Am.*, 61: 285-290 (1968).
Damayanti et al. "Effect of plant extracts and systemic fungicide on the pineapple fruit-rotting fungus, *Ceratocystis paradoxa*." Cytobios, 86(346):155-65 (1996).
Ge and Weston, "Ovipositional and feeding deterrent from Chinese prickly ash against Angoumois grain moth (Lepidoptera: Gelechiidae)." *J. Econ. Entomol.*; 88: 1771-1775 (1995).
Gonzalez-Coloma et al., "Silphinene Derivatives: Their Effects and Modes of Action on Colorado Potato Beetle." *J Agric Food Chem*, 45: 946-950 (1997).
Gonzalez-Coloma et al., "Antifeedant and toxic effects of sesquiterpenes from *Senecio palmenes* to Colorado potato beetle." *J Chem Ecol*, 21: 1255-1270 (1995).
Gouamene-Larnine et al., Differential susceptibility to abamectin and two bioactive avermectin analogs in abamectin-resistant and -susceptible strains of Colorado potato beetle, *Leptinotarsa decemlineata* (Say) (Coleoptera: Chrysomelidae). *Pestic Biochem Phys*, 76: 15-23 (2003).
Grafius, "Economic Impact of Insecticide Resistance in the Colorado Potato Beetle (Coleoptera: Chrysomelidae) on the Michigan Potato Industry." *Econ Entomol* 90: 1144-1151 (1997).
Green et al. "Phenolic compounds on the pod-surface of pigeonpea, *Cajanus cajan*, mediate feeding behavior of *Helicoverpa armigera* larvae." J Chem Ecol. 29(4):811-21 (2003).
Haffani et al., "*Bacillus thuringiensis* cry3Ca1 Protein is Toxic to the Colorado Potato Beetle, *Leptinotarsa decemlineata* (Say)." *Biotechnol Prog*, 17: 211-216 (2001).
Hampton et al., "Comparative chemical attributes of native North American Hop, *Humulus lupulus* var. *lupuloides* E. Small." *Phytochemistry*, 61: 855-862 (2002).
Hare, J.D., "Ecology and management of the Colorado potato beetle." *Annu. Rev. Entomol.*, 35:81-100 (1990).
Hill and Roelofs, "Sex Pheromone components of the obliquebanded leafroller moth (*Choristoneura rosaceana*)." *J. Chem. Ecol.*, 5: 3-11 (1979).
Isman et al., "Insect antifeedants." *Pesticide Outlook*: 152-156 (2002).
Jermy et al., "Host plant finding in phytophagous insects: the case of the Colorado potato beetle." Entomol Exp Appl, 49:83-98 (1988).
Johri et al., "Ovicidal action and feeding response of certain plant extracts against *Bagrada cruciferarum* (Kirk), *Pieris Brassicae* (Linn.) and *Mylabris pustulata* (Thunb)." J. Appl. Zool. Res. 15: 37-42 (2004).
Jones et al., "Repellent and oviposition-deterring effects of hop beta-acids on the two-spotted spider mite *Tetranychus urticae*." *Pestic Sci*, 47: 165-169 (1996).

(Continued)

*Primary Examiner* — Michael Meller
(74) *Attorney, Agent, or Firm* — Medlen & Carroll, LLP

(57) ABSTRACT

The present invention provides compositions and methods for controlling plant pests. In particular, the present invention provides plant extracts with insecticidal activity.

1 Claim, 4 Drawing Sheets

OTHER PUBLICATIONS

Jones et al., "Integrated Management of Two-spotted Spider Mite *Tetranychus urticae* on Hops using Hop β-acids as an Antifeedant Together with the Predatory Mite *Phytoseiulus persimilis*." Biocontrol Sci. Technol., 13:241-252 (2003).

Katsiotis et al., "Composition of the essential oils from the leaves of various *Humulus lupulus* L. Cultivars." *Flavour Frag.* J., 5; 97-100 (1990).

Kawazu et al. "*Xanthumin* and 8-epi-xanthatin as insect development inhibitors from *Xanthium canadense* Mill." Experientia 35(10):1294-5 (1979).

Koul et al. "Antifeedant Effect of the Limonoids from *Entandrophragma candolei* (Meliaceae) on the Gram Pod Borer, *Helicoverpa armigera* (Lepidoptera: Noctuidae)." J Agric Food Chem. 51(25):7271-5 (2003).

Krupke et al., "Field Attraction of the Stink Bug *Euschistus conspersus* (Hemiptera: Pentatomidae) to Synthetic Pheromone-Baited Host Plants." *J. Econ. Entomol.*, 94:1500-1505 (2001).

Larocque et al., "Effects of tansy essential oil from *Tanacetum vulgare* on biology of oblique-banded leafroller, *Choristoneura rosaceana*." *J. Chem. Ecol.*, 25: 1319-1330 (1999).

Latrasse et al., "Composition and major odorous compounds of the essential oil of *Bifora radians*, an aldehyde-producing weed." *J. High Resolution Chrom.*, 14:549-553 (1991).

Mailloux et al., "Density yield relationships and economic injury level model for the Colorado potato beetle larvae on potatoes ." *Res Popul Ecol*, 33:101-113 (1991).

Mancebo et al., "Antifeedant activity of *Quassia amara* (Simaroubaceae) extracts on *Hypsipyla grandella* (Lepidoptera: Pyralidae) larvae." *Crop Prot.*, 19: 301-305 (2000).

Martin et al., "Two new bacterial pathogens of Colorado potato beetle Coleoptera: Chrysomelidae." *J Boon Entomol*, 97: 774-780 (2004).

Mauchline et al., "The effects of non-host plant essential oil volatiles on the behaviour of the pollen beetle *Meligethes aeneus*." *Entomol. Exp. Appl.*, 114: 181-188 (2005).

Mendel et al., "Antifeedant effects of citrus limonoids differing in A-ring structure on Colorado potato beetle (Coleoptera: Chrysomelidae) larvae." *J Econ Entomol*, 84: 1158-1162 (1991).

Miller and Cowles, "Stimulo deterrent diversion: A concept and its possible application to onion maggot control." *J. Chem. Ecol.*, 16:3197-3212 (1990).

Mitchell and McCashin, "Tasting green leaf volatiles by larvae and adults of Colorado potato beetle, *Leptinotarsa decemlineata*." *J Chem Ecol*, 20: 753-769 (1994).

Mordue et al., "Actions of azadirachtin, a plant allelochemical, against insects." *Pesticide Science*, 54: 277-284 (1998).

Nathan et al. "Efficacy of *Melia azedarach* L. Extract on the Malarial Vector *Anopheles stephensi* Liston (Diptera: Culicidae)." Bioresour Technol. (2005).

Nauen and Denholm, "Resistance of insect pests to neonicotinoid insecticides: Current status and future prospects." *Arch Insect Biochem.*, 58: 200-215 (2005).

Noling et al., "Joint Influence of *Pratylenchus penetrans* (Nematoda) and *Leptinotarsa decemlineata* (Insecta) on *Solanum tuberosum* Productivity and Pest Population Dynamics." *J Nematol*, 16: 230-234 (1984).

Pare and Tomlinson, "Induced synthesis of plant volatiles." *Nature*, 385: 30-31 (1997).

Perlak et al., "Genetically improved potatoes: protection from damage by Colorado potato beetles." *Plant Mol Biol*, 22: 313-321 (1993).

Pickett et al., "Developing sustainable pest control from chemical ecology." *Agric. Ecosyst. Environ.*, 64: 149-156 (1997).

Rodriguez et al. "A new tetranortriterpenoid from *Trichilia havanensis*." J Nat Prod. 66(3):452-4 (2003).

Roelofs and Arn, "Sex attractant of the red-banded leaf roller moth." *Nature*, 219: 513 (1968).

Roelofs and Tette, "Sex pheromone of the oblique-banded leaf roller moth." *Nature*, 226: 1172 (1970).

Roelofs et al., "Sex pheromone components of the redbanded leafroller, *Argyrotaenia velutinana* (Lepidoptera tortricidae)."*J. Chem. Ecol.*, 1: 83-89 (1975).

Sampson et al. "Insecticidal Activity of 23 Essential Oils and Their Major Compounds Against Adult *Lipaphis pseudobrassicae* (Davis) (Aphididae: Homoptera)." Pest Manag Sci. 61(11):1122-8 (2005).

Schutz et al., "Host plant selection of the Colorado potato beetle as influenced by damage induced volatiles of the potato plant." *Naturwissenschaften*, 84: 212-217 (1997).

Scott et al., "Botanical insecticides for controlling agricultural pests: piperamides and the Colorado Potato Beetle *Leptinotarsa decemlineata* say (Coleoptera: Chrysomelidae)." *Arch Insect Biochem*, 54: 212-225 (2003).

Stankovic et al., "Colorado potato beetle [*Leptinotarsa decemlineata* (Say)] resistance to organophosphates and carbamates in Serbia." *J Pest Sci*. 77: 11-15 (2004).

Stelinski et al., "Presence of long-lasting peripheral adaptation in the obliquebanded leafroller, *Choristoneura rosaceana* and absence of such adaptation in the redbanded leafroller, *Argyrotaenia velutinana.*" *J. Chem. Ecol.*, 29: 403-422 (2003).

Stelinski et al., "Concentration of air-borne pheromone required for long-lasting peripheral adaptation in the obliquebanded leafroller, *Choristoneura rosaceana* (Harris)." *Physiol. Entomol.*, 28:97-107 (2003).

Stelinski et al., "Increased EAG responses of tortricid moths after prolonged exposure to plant volatiles: evidence for octopamine-mediated sensitization." *J. Insect Physiol.*, 49: 845-856 (2003).

Strickler and Whalon, "Microlepitoptera species composition in Michigan apple orchards." *Environ. Entomol.*, 14: 486-495 (1985).

TimTec LLC, 301-A Harmony Business Park, Newark, Delaware, 19711. *Humulus* lupulus extract. (http://www.timtec.net/products/plant_extracts.htm; currently http://timtec.net/Plant-Extracts.html) Sep. 12, 2005.

Turker and Camper, "Biological activity of common mullein, a medicinal plant." J Ethnopharmacol. 82(2-3):117-25 (2002).

Zhao et al., "Inheritance and synergism of resistance to imidacloprid in the Colorado potato beetle (Coleoptera: Chrysomelidae)." *J Econ Entomol* 93: 1508-1514 (2000).

* cited by examiner

Figure 4

Table 9. The contact toxicities of plant extracts to various development stages of Colorado potato beetle after 48 h incubation. Values in a column followed by the same letter are not significantly different (P<0.05).

| Treatment | 1st Instar Larvae % Mortality±SEM | 2nd Instar Larvae % Mortality±SEM | 3rd Instar Larvae % Mortality ± SEM | 4th Instar Larvae % Mortality ± SEM | Adult % Mortality ±SEM |
|---|---|---|---|---|---|
| Control | 2.24±0.97 c | 2.24±0.97 c | 0.97±0.56 c | 0.00±0.00 c | 0.00±0.00 c |
| Artemisia vulgaris | 11.14±0.57 c | 8.16±0.18 c | 7.79±0.56 c | 10.93±0.82 b | 24.69±0.55 ab |
| Chenopodium album | 3.29±1.56 c | 11.57±0.11 c | 0.97±0.56 c | 4.99±0.11 bc | 16.36±0.37 ab |
| Hedera helix | 11.57±0.11 c | 11.57±0.11 c | 16.36±0.39 c | 12.21±1.33 b | 7.79±0.57 bc |
| Humulus lupulus | 78.38±0.09 b | 73.48±0.26 b | 83.79±0.59 b | 39.96±0.15 a | 11.14±0.57 abc |
| Lolium temulentum | 9.59±0.43 c | 13.24±0.11 c | 11.14±0.57 c | 5.64±2.54 bc | 5.18±1.01 bc |
| Salvia officinalis | 11.14±0.57 c | 13.24±0.11 c | 12.56±0.87 c | 11.14±0.57 b | 3.29±1.56 bc |
| Sambacus nigra | 13.24±0.11 c | 8.16±0.18 c | 8.16±0.18 c | 11.57±0.11 b | 3.29±1.56 bc |
| Verbascum spp | 19.58±0.63 c | 8.16±0.18 c | 6.87±2.99 c | 9.59±0.43 b | 8.16±0.18 bc |
| Xanthium strumarium | 5.64±2.54 c | 6.49±0.18 c | 4.25±2.26 c | 7.79±0.57 bc | 14.39±0.78 bc |
| Imidacloprid | 100±0.00 a | 94.82±3.05 a | 100±0.00 a | 11.57±0.11 b | 44.37±3.32 a | ced
INSECTICIDAL COMPOSITIONS AND USES THEREOF

FIELD OF THE INVENTION

The present invention provides compositions and methods for controlling plant pests. In particular, the present invention provides plant extracts with insecticidal activity.

BACKGROUND

Agricultural pests are a major source of lost revenue for commercial growers. Pest are generally crop and region specific. One exemplary pest is the obliquebanded leafroller, *Choristoneura rosaceana* (Harris) (*Lepidoptera*: Tortricidae), a tortricid moth native to North America and widely distributed from British Columbia to Nova Scotia and south to Florida (Chapman et al. 1968, Ann. Entomol. Soc. Am. 61: 285-290). The obliquebanded leafroller has an extremely wide host range; however, its host preference is limited to woody plants including Rosaceae. It is an established pest of pome fruits throughout North America, particularly apples. The redbanded leafroller, *Argyrotaenia velutinana* (Walker) (*Lepidoptera*: Tortricidae), is sympatric with the obliquebanded leafroller and native to temperate eastern North America (Chapman 1973, Annu. Rev. Entomol. 18: 73-96). The host range of this species is even broader than that of the obliquebanded leafroller; it feeds on leaves of diverse plant species excluding conifers. Redbanded leafroller larvae feed on many unrelated plants, including most common fruits, vegetables, weeds, flowers, ornamentals and shrubs. Among the fruits, redbanded leafrollers prefer apples and are common pest in the apple-growing areas of the midwestern and eastern United States and eastern and western Canada. Its pest status has been associated with commercial use of pesticides and nutrient adjuvants in upper midwestern orchards (Strickler and Whalon 1985, Environ. Entomol. 14: 486-495).

Another important agricultural pest is the Colorado potato beetle. The Colorado potato beetle (CPB), *Leptinotarsa decemlineata* (Say.), is the most destructive pest of potatoes worldwide (Hare, Annu Rev Entomol 35:81-100 (1990); Zehnder and Gelernter, J Econ Entomol 82: 756-761 (1989)). CPB potato herbivory has been studied by many researchers (Ferro et al., J Econ Entomol 76: 349-356 (1983); Noling et al., J Nematol 16: 230-234 (1984); Mailloux et al., Res Popul Ecol 33: 101-113 (1991); Zehnder et al., J Econ Entomol 88: 155-161 (1995)) and pest management has been implemented using various control strategies, especially chemical control. Reliance on pesticide suppression, coupled with the beetles' propensity to evolve resistance and cross resistance has greatly exacerbated CPB management (Stankovic et al., J Pest Sc 77: 11-15 (2004)). Potato producers in the Upper Midwest have experienced intense economic and production challenges since the mid-1940's due to CPB resistance evolution (Grafius, J Econ Entomol 90: 1144-1151 (1997)). Introduction of neonicitinoid insecticides in the early 1990's averted impending disaster for the potato industry from the last resistance episode (Grafius, J Econ Entomol 90: 1144-1151 (1997)). Recently, resistance and cross resistance to the neonicitinoids is again flaring in the upper Midwest and East coast (Zhao et al., J Econ Entomol 93: 1508-1514 (2000); Nauen and Denholm, Arch Insect Biochem 58: 200-215 (2005)). Given resistance evolution, the search for promising CPB management tools continues. Thus, what is needed in the art are additional insecticides.

SUMMARY OF THE INVENTION

The present invention provides compositions and methods for controlling plant pests. In particular, the present invention provides plant extracts with insecticidal activity.

For example, in some embodiments, the present invention provides a plant extract (e.g., derived from *A. vulgaris, H. helix, H. lupulus, L. temulentum, R. tinctoria, S. officinalis, S. nigra, U. dioica, Verbascum* spp., *X. strumarium, C. album, R. lutea, S. nigrum, Bifora radians, lappa*, or *C. maculatum*), wherein the plant extract exhibits biopesticide activity. In some embodiments, the biopesticide activity is insecticide activity, insect repellent activity or insect antifeedant activity. In certain embodiments, the plant extract exhibits biopesticide activity against *Leptinotarsa decemlineata*.

The present invention further provides a method, comprising, providing a plant extract. (e.g., derived from *A. vulgaris, H. helix, H. lupulus, L. temulentum, R. tinctoria, S. officinalis, S. nigra, U. dioica, Verbascum* spp., *X. strumarium, C. album, R. lutea, S. nigrum, Bifora radians, A. lappa*, or *C. maculatum*); and contacting the plant extract with a plant of interest under conditions such that the plant extract exhibits biopesticide activity. In some embodiments, the biopesticide activity is insecticide activity, insect repellent activity or insect antifeedant activity. In some embodiments, the plant extract exhibits biopesticide activity against *Leptinotarsa decemlineata*. In some embodiments, the plant of interest is a crop plant, such as for example, a food crop (e.g., potato). In certain embodiments, the method further comprises the step of contacting the plant with a known pesticide.

In yet other embodiments, the present invention provides a plant extract (e.g., derived from *B. radians* or *X. strumarium*), wherein the plant extract exhibits bio-attractant activity. In some embodiments, the bio-attractant activity attracts a leafroller (e.g., a male obliquebanded leafroller, a female obliquebanded leafroller, a male redbanded leafroller, or a female redbanded leafroller).

In yet other embodiments, the present invention provides a method, comprising, providing a plant extract (e.g., derived from *B. radians* or *X. strumarium*); and contacting the plant extract with a plant of interest or an object of interest (e.g., trap) under conditions such that the plant extract exhibits bio-attractant activity. In some embodiments, the bio-attractant activity attracts a leafroller (e.g., a male obliquebanded leafroller, a female obliquebanded leafroller, a male redbanded leafroller, or a female redbanded leafroller). In some embodiments, the plant of interest is a crop plant (e.g., a food crop). In certain embodiments, the food crop is a pome fruit (e.g., apple). In certain embodiments, the method further comprises the step of contacting the plant with a known pesticide.

The present invention additionally provides a plant extract (e.g., derived from *B. radians* or *A. lappa*), wherein the plant extract exhibits anti-oviposition activity. In some embodiments, the anti-oviposition activity is effective against a leafroller (e.g., a female obliquebanded leafroller or a female redbanded leafroller).

The present invention also provides a method, comprising, providing a plant extract (e.g., derived from *B. radians* or *A. lappa*); and contacting the plant extract with a plant of interest under conditions such that the plant extract exhibits anti-oviposition activity. In some embodiments, the anti-oviposition activity is effective against a leafroller (e.g., a female obliquebanded leafroller or a female redbanded leafroller). In some embodiments, the plant of interest is a crop plant (e.g., a food crop). In certain embodiments, the food crop is a pome fruit (e.g., apple). In certain embodiments, the method further comprises the step of contacting the plant with a known pesticide.

The present invention additionally provides a method of generating a plant extract comprising, providing a plant (e.g., *A. vulgaris, H. helix, H. lupulus, L. temulentum, R. tinctoria, S. officinalis, S. nigra, U. dioica, Verbascum* spp., *X. strumarium, C. album, R. lutea, S. nigrum, Bifora radians, A. lappa,* or *C. maculatum*), homogenizing the plant; and extracting the resulting homogenate with methanol.

DESCRIPTION OF THE FIGURES

FIG. 4 shows Table 9.

DEFINITIONS

Figure 1:
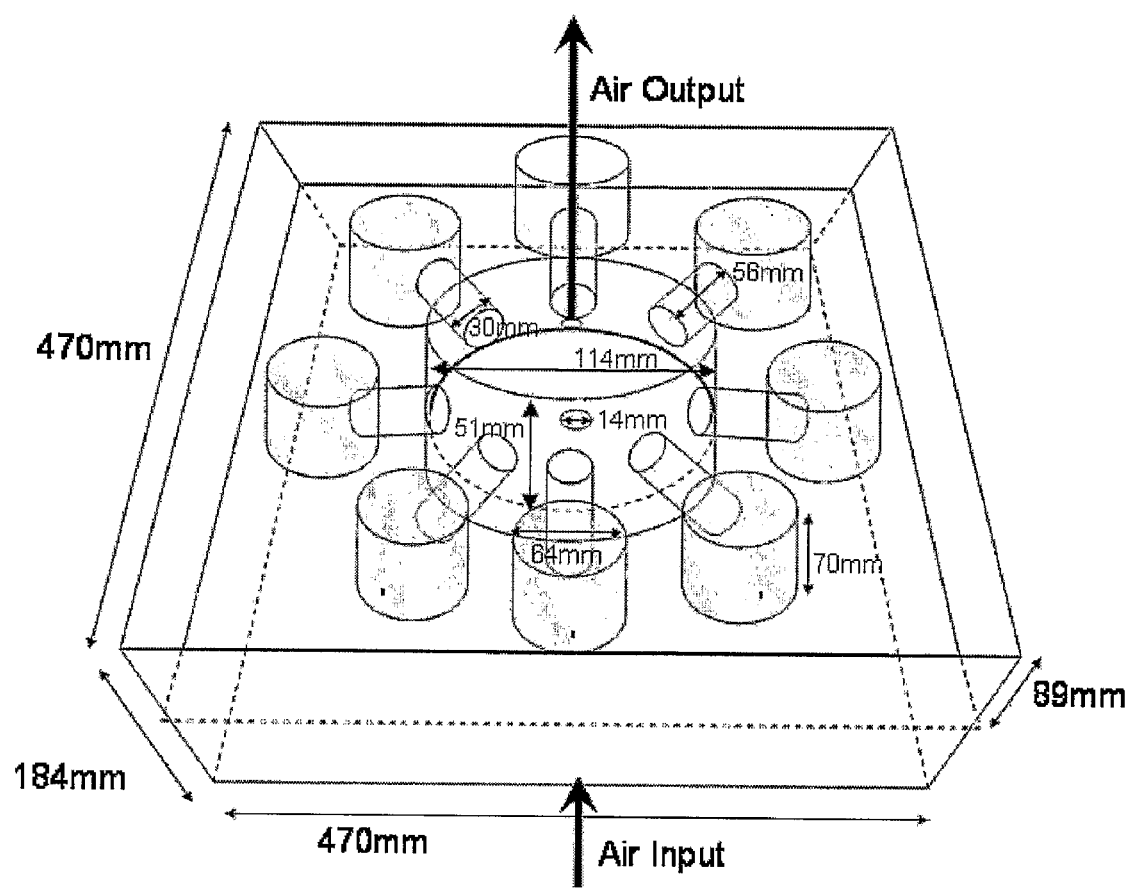
FIG. 1 shows a diagram of eight arm olfactometer used to assay responses of male and female obliquebanded leafrollers, *Choristoneura rosaceana*.

As used herein, the term "plant host" refers to a plant or plant part. As used herein, the term "plant part" refers to any portion of a plant or plant substructure, including, but not limited to, leaves (detached or non-detached), roots, stems, fruits, flowers, or protoplast and cell cultures.

As used herein, the term "pesticide" refers to any substance or mixture of substances that prevent, destroy, repel, or mitigate any pest. In some embodiments, the term pesticide applies to insecticides, repellants, anti-feeding agents, herbicides, fungicides, and various other substances used to control pests.

As used herein, the terms "insecticide" and "insecticides" refer to compositions that kill insects or otherwise deter insects from feeding.

As used herein, the term "antifeedant" refers to a composition that prevents an insect or other pest from feeding.

As used herein, the terms "repellent" and "repellents" refer to a composition that repels pests, including insects.

As used herein, the term "biopesticide" refers to a pesticide derived from such natural materials as animals, plants, bacteria, and certain minerals.

As used herein, the term "biochemical" refers to a chemical that occurs naturally in an organism, or an identical substance that has been made artificially.

As used herein, the term "biochemical pesticide" refers to a naturally-occurring substance that controls pests. In some embodiments, biochemical pesticides control pests by insecticidal activity. In other embodiments, biochemical pesticides control pests by a mechanism other than toxicity. Examples include, but are not limited to, sex pheromones that are used as mating disrupters for insect pests, and plant extracts that are used as attractants to lure insect pests to traps or that are used as insect repellents.

As used herein, the term "insecticidally effective amount," when used in reference to a composition of the present invention, refers to the amount of the composition (e.g., plant extract) necessary to kill an insect or otherwise deter the feeding of an insect from the source. When an insect comes into contact with a insecticidally effective amount of a composition, the results are typically death of the insect, or the insects do not feed upon the source which comprises the composition.

"Biologically active", as used herein, refers to a molecule having the structural, regulatory, or biochemical functions of a naturally occurring molecule.

"Industrial crop", as used herein, refers to crops grown primarily for consumption by humans or animals or use in industrial processes (for example, as a source of fatty acids for manufacturing or sugars for producing alcohol). It will be understood that either the plant or a product produced from the plant (for example, sweeteners, oil, flour, or meal) can be consumed. Examples of food crops include, but are not limited to, corn, soybean, rice, wheat, oilseed rape, cotton, oats, barley, and potato plants.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in viva. For example, host cells may be located in a transgenic animal or plant.

The term "sample" as used herein is used in its broadest sense. For example, a sample from a plant includes plant extracts and purified plant components or biological molecules.

General Description

The obliquebanded leafroller and the redbanded leafroller are closely related species, sharing the major components of their pheromone blends: (Z)11-14:Ac and (E)11-14:Ac in a 98:2 ratio for obliquebanded leafroller and 93:7 ratio for redbanded leafroller (Roelofs and Am 1968, Nature 219: 513; Roelofs and Tette 1970, Nature 226: 1172; Roelofs et al. 1975, J. Chem. Ecol. 1: 83-89; Cardé and Roelofs 1977, J. Chem. Ecol. 3: 143-146; Hill and Roelofs 1979, J. Chem. Ecol. 5: 3-11). In addition, both species' antennae respond to green leaf volatiles and terpenoids as measured by electroantennograms (EAGs). Such plant volatiles are likely important cues utilized by males and females of both species for host-plant location.

Several plant extracts have been identified containing secondary plant compounds including, waxes, terpenes, steroids, alkaloids, phenolics and cardiac glycosides, which affect various behaviors of insects belonging to different families (Mordue et al. 1998, Pestic. Sci. 54: 277-284; Ge and Weston 1995, J.-Econ. Entomol.; 88: 1771-1775; Blaney et al. 1988, Entomol. Exp. Appl. 46: 267-274; Mancebo et al. 2000, Crop Prot. 19: 301-305; Bruno et al. 2003, Biochem. Syst. Ecol. 31: 1051-1056). In some embodiments, the plant derived compounds are used in "push-pull" methods of pest control (Miller and Cowles 1990, J. Chem. Ecol. 16: 3197-3212; Pickett et al. 1997, Agric. Ecosyst. Environ. 64: 149-156). As part of this strategy, plant-derived repellents, antifeedants, or oviposition deterrents impart the "push" by moving pests away from the targeted crop (Mauchline at al. 2005, Entomol. Exp. Appl. 114: 181-188; Bartelt et al. 2004, J. Chem. Ecol. 30: 913-925; Kahn et al. 2001, Insect Sci. Appl. 21: 375-380). The plant species used in experiments conducted during the course of development of the present invention were chosen because they are known to produce secondary compounds such as monoterpenes, sesquiterpenes and triterpenes (Katsiotis et al. 1990, Flavour Frag. J. 5: 97-100; Latrasse et al. 1991, J. High Resolution Chrom. 14: 549-553; Baser et al. 1995, J. Essent. Oil. Res. 10: 451-452) which affect the behavior of arthropods (Krupke et al. 2001, J. Econ. Entomol. 94: 1500-1505; Jones et al. 2003, Biocontrol Sci. Techn. 13: 241-252). These plants occur in the North American range of both leafroller species used in experiments conducted during the course of development of the present invention. In Turkey, these plant species are associated with apple-orchard agroecosystems, but tortricid moths have not been observed feeding on them. In addition, some of these plants are insect anti-feedants and repellents (Johri et al. 2004, J.-Appl.-Zool.-Res. 15: 37-42). Therefore, the effects of these plant species was evaluated on two important leafroller pests of apples in North America.

All of the plant extract samples elicited significant EAG responses from male and female obliquebanded leafrollers and redbanded leafrollers. Thus, the antennae of these two tortricid species respond to certain constituents of these plant extracts, which may be important in host-plant location or avoidance. There was sexual dimorphism in EAG response to the majority of the plant extracts assayed. Specifically, males of both species showed greater EAG responses to plant extracts compared with females. A previous study has shown that the antennal sensillae of male and female obliquebanded leafrollers and redbanded leafrollers are sensitive to a wide array of green leaf and fruit volatiles that might serve as cues in host-plant finding for these polyphagous herbivores (Stelinski et al. 2003, J. Insect Physiol. 49: 845-856).

Behavioral assays demonstrated that male obliquebanded leafrollers exhibit attraction to two of the plant extracts tested: *X. strumariuma* and *B. radians*. Female obliquebanded leafrollers were also attracted to *X. strumariuma*. The highest level of attraction for both sexes was observed with *X. strumariuma*, which also elicited the largest EAG responses. It is contemplated that *X. strumariuma* produces a kairomone attractive to obliquebanded leafroller males and females that finds use as a bisexual lure for monitoring this insect.

Oviposition studies demonstrated that female obliquebanded leafrollers distinguished between plant extract-treated versus control wax paper, generally avoiding the extract treatments.

In experiments conducted during the course of development of the present invention, *B. radians* extract completely deterred oviposition of female obliquebanded leafrollers and *A. lappa* also significantly reduced the number of eggs laid on the treated paper. Larocque et al. (1999, J. Chem. Ecol. 25: 1319-1330) reported significant oviposition deterrence for female obliquebanded leafrollers with *Tanacetum vulgare*. Oviposition deterrent effects of the currently-investigated non host-plant extracts demonstrate their use in managing this apple pest by employing a "push-pull" strategy. The antioviposition effects of *B. radians* find use in "pushing" female obliquebanded leafrollers away from oviposition sites, while the attractiveness of *X. strumariuma* is exploited against male and female obliquebanded leafrollers.

Additional experiments conducted during the course of development of the present invention identified plant extracts with toxicities against Colorado potato beetle. In contact toxicity tests, a range of plant extract toxicities were observed with Colorado potato beetle larvae from 30 indigenous plants.

In experiments conducted during the course of development of the present invention, $3^{rd}$ instar Colorado potato beetle larvae were found to be susceptible to an array of plant extracts. This developmental stage was chosen since previous studies (Hilton et al. 1998, Can Entomol 130: 187-194; Haffani et al. 2001, Bitechnol Prog 17: 211-216; Martin et al. 2004, J Econ Entomol 97: 774-780) demonstrated that $3^{rd}$ instar larvae were susceptible to certain insecticides. This stage is also the most destructive stage of Colorado potato beetle (Perlak et al. 1993, Plant Mol Biol 22: 313-321).

Crude plant extracts demonstrated greater toxicities in the contact assays than in feeding assays. For example, *H. lupulus* was the most toxic plant extract in contact assays, yet it showed moderate toxicity in the feeding assays. Similar results were reported by Hilton et al. (1998, supra) who showed that cypermethrin contact effect was greater than its residual effect. Thus insects in the contact assays may have died earlier than those in residual assays yielding the opportunity for prolonged exposure. Martin et al. (2004) waited 96 h before recording the numbers of Colorado potato beetle which had been killed by *Photorhabdus luminescens* and Haffani et al. (2001, supra) employed a 6 day incubation period when examining the effectiveness of *Bacillus thruringieisis*.

In contact assays, *H. lupulus* crude extract caused 91.1% and 99.4% mortalities after 24 and 48 hr respectively. These results demonstrated that *H. lupulus* crude extract is as effective as currently used insecticides.

Certain experiments conducted during the course of development of the present invention analyzed contact and residual toxicities of plant extracts to $3^{rd}$ instar Colorado potato beetle larvae. Some of the crude plant extracts were toxic to beetle larvae and find use in controlling the pest under field conditions.

Further experiments conducted during the course of development of the present invention exposing CPB developmental stages to selected plant extracts. Plant extracts elicited wide variability in toxicity to CPB larvae and adults.

The experiments clarified previous observations (Scott et al., Arch Insect Biochem 54: 212-225 (2003)) that the first three stages of Colorado potato beetle are more sensitive to morbidity agent including plant extracts. Second and third instar larvae were previously reported to be the most susceptible stages in the life cycle of Colorado potato beetle to some insecticides, plant extracts and biological control agents (Zehnder and, J Econ Entomol 82: 756-761 (1989); Scott et al., J Chem Ecol 29: 2761-2776 (2003); Hilton et al., Can Entomol 130: 187-194 (1998); Martin et al., J Econ Entomol 97: 774-780 (2004)). In addition to other putative tolerance mechanisms (aging, metabolism, mobilization of defense systems, target site changes, etc.) lower tolerance of 1-3 instar larvae may be related to their changing cuticular structure since the physical and chemical properties of cuticles excised from the various developmental stages are different. Thus cuticular changes may also affect the absorption and transportation to active sites of plant extracts. Therefore, the relatively thin cuticle of the first three instar compared to $4^{th}$ instar may contribute to their sensitivity to plant extracts. The fourth stage was relatively less susceptible to plant extracts. CPB adults were not as sensitive to plant extract as the larvae. Adult tolerance to plant extracts and insecticides has been previously reported by Scott et al. (supra) who found that adults were 10-fold less susceptible to *Piper tuberculatum* extract than the early instar larvae and by Gouamene-Lamine et al. (Pestic Biochem Phys 76: 15-23 (2003)), who demonstrated that Abamectin was less toxic to adult Colorado potato beetle than to the larvae. The present invention is not limited to a particular mechanism. Indeed, an understanding of the mechanism is not necessary to practice the present invention. Nonetheless, it is contemplated that this sharp mortality decrease in the adult stage could be related to difference in the elytra which putatively make it more difficult for the plant extracts to get to active sites internally. In addition, adults are reported to have nearly three fold more cytochrome P-450 than larvae such that they might be able to detoxify plant extract faster than larvae do (Gouamene-Lamine et al., supra).

The dosage-mortality study demonstrated that *H. lupulus* extract caused larvae and adult mortality in 48 h under laboratory conditions. The dosage-mortality study demonstrated a differential response across each developmental stage to the plant extract. $LC_{50}$ and fucidial limits values of the different stages of Colorado potato beetle showed that the adults were the least sensitive among the tested stages to *H. lupulus* toxicity while the first, second and third instar larvae were the most susceptible to the plant extract and the fourth instar was intermediate in sensitivity.

This study demonstrated that *H. lupulus* finds use as a natural plant product against Colorado potato beetle in pest management programs. In some embodiments, *H. lupulus* extracts are used alone or in combination with conventional insecticides. In other embodiments, the incorporation of hop extracts as a component of CPB management programs increases the use-life of insecticides like the neonicotinoids through redundant killing on resistance management. It is contemplated that the mixture of plant extract analogues is more active than a single compound and delays the development of resistance in CPB.

Additional experiments conducted during the course of development of the present invention demonstrated that behavior of *L. decemlineata* is reduced by extracts of the five plants tested. Disruption of feeding by *L. decemlineata* did not increase linearly with increasing concentration of these extracts. Rather, beetles were either able to feed, as seen in the leaves without any extract added and those with 0.2% concentration extracts added, or they were prevented from feeding.

The tested plants contain monoterpenes, sesquiterpene lactones and triterpenes, and some of these plant species have been shown to induce various activities in insects, including repellency, antifeedancy and morbidity (Heywood et al., The biology and chemistry of the compositae. Academic, London (1977); Osvath et al., Herba Hungarica 21: 141-147 (1982); Çetinsoy et al., Turk J of Agric Forest 22: 543-552 (1998)). The present invention is not limited to a particular mechanism. Indeed, an understanding of the mechanism is not necessary to practice the present invention. However, it is contemplated that the antifeedant activity of the tested plant extracts observed in this experiment is related to the presence of specific compounds or mixtures of different compounds present in each plant. It is known that the pyrrolizidine alkaloids (acethylrachelanthamine), cardiopetatnines, terpenoids, cucurbitacins, silphinenes and limonoids have shown deterrence to the Colorado potato beetle (Bentley et al., Entomol Exp Appl 49: 189-193 (1988); Bentley et al., J Agric Food Chem 38: 1400-1403 (1990); Gonzalez-Coloma et al., J Chem Ecol 21: 1255-1270 (1995); Gonzalez-Coloma et al., J Agric Food Chem 45: 946-950 (1997); Mendel et al., J Econ Entomol 84: 1158-1162 (1991); Scott et al., Arch Insect Biochem 54: 212-225 (2003)).

Plant damage resulting from insect feeding results in the release of plant volatiles, mainly terpenes, which help herbivores locate their hosts (Pare and Tumlinson, Nature 385: 30-31). The Colorado potato beetle is a specialist of some Solanaceae species and host-finding and selection by Colorado potato beetle have been studied (Hsiao et al., Entomol Exp Appl 12: 777-788 (1969); Mitchell and McCashin, J Chem Ecol 20: 753-769 (1994); Jermy et al., Entomol Exp Appl 49: 83-98 (1988); Schutz et al., Naturwisssenschaften 84: 212-217 (1997)). These studies have shown that chemicals in the plant are key factors in selection of host plants, and the distribution of attractants and phagostimulants play an important role in this process. Larvae, especially younger larvae, appeared to be more sensitive than 4th instar larvae and adults to phagostimulants produced by plants (Jermy et al., Insect Sci Appl 1: 237-242 (1981)). The biting and feeding action of larvae were induced by specific plant chemicals and these phagostimulants are required for continuous feeding (Hsiao et al., supra). The results of experiments conducted during the course of development of the present invention demonstrated that most plant extracts at lower concentration (0.2% (w/w)) concentration did not sufficiently inhibit the beetles' responses to these specific stimuli, as the number of times the larvae fed on leaf tissue was unaffected. At higher concentrations, many of the extracts inhibited, or completely prevented, feeding by larvae indicating that the concentrations of volatile and non-volatile plant chemicals in the extracts were sufficient to prevent recognition of the host plant over the course of these assays.

The results showed that there is a chemical basis for the antifeedant properties of tested plant extracts, since feeding intensity decreased with increasing concentration of plant extracts. Desensitization to antifeedants in no-choice assays has been documented in lepidopteran larvae (Bomford and Isman, Entomol Exp Appl 81: 301-313 (1996); Isman et al., Pesticide Outlook August 2002: 152-156 (2002) in which feeding deterrence declines with exposure time. The plant derived compounds xanhotoxin or thymol was active at repelling *Pseudaletia unipuncta* from feeding on host plant tissues, but their deterrent activity reduced after 4-6 h. A similar decline in activity was seen for the pure compound azadirachtin but not for the mixture of neem extract. In experiments conducted during the course of development of the present invention using plant extracts, larvae remained active on the untreated leaves and on those with the lowest concentrations of extracts, whereas feeding was prevented throughout the 24 hours of the observations on leaves treated with the higher concentrations of these mixtures. This indicates that there is limited potential for desensitization of *L. decemlineata* larvae to the plant extracts tested.

DETAILED DESCRIPTION OF THE INVENTION

Pests are living organisms that live where they are not wanted or that cause damage to crops or humans or other animals. Examples of pests include insects, mice and other animals, unwanted plants (weeds), fungi, and microorganisms such as bacteria and viruses. A pesticide is any substance or mixture of substances intended for preventing, destroying, repelling, or mitigating any pest, including insecticides, herbicides, and fungicides. Under United States law, a pesticide is also any substance or mixture of substances intended for use as a plant regulator, defoliant, or desiccant.

The EPA exempts biological control agents, except for certain microorganisms, from regulation. (Biological control agents include beneficial predators such as birds or ladybugs that eat insect pests). Products that contain certain low-risk ingredients, such as garlic and mint oil, have been exempted from Federal registration requirements, although State regulatory requirements may still apply.

There are many types of pesticides available for controlling pests. Categories include biopesticides, antimicrobials, and pest control devices with many specific categories for types of pests, i.e. acaricides, larvicide, and the like. A variety of broad and specific application pesticides are available from commercial sources. By their very nature, most pesticides create some risk of harm because they are designed to kill or otherwise adversely affect living organisms. At the same time, pesticides are useful to society. Pesticides can kill potential disease-causing organisms and control insects, weeds, and other pests.

Biologically based pesticides, such as pheromones and microbial pesticides, are becoming increasingly popular and often are safer than traditional chemical pesticides. In addition, EPA is registering increasing numbers of reduced-risk conventional pesticides. However, prior to the present invention, biologically based pesticides did not have the potency, e.g., effectiveness, or immediacy of action required to substantially reduce the economic damage of the target pests.

Therefore, in order to balance benefits v. safety, currently the focus of procedures to address pest control uses Integrated Pest Management (IPM) systems. IPM is the use of pest and environmental information in conjunction with available pest control technologies to prevent unacceptable levels of pest damage by the most economical means and with the least possible hazard to persons, property and the environment. IPM includes combining environmentally safer but less effective compositions and methods to achieve optimum pest control at the same time increasing the safety of pest control measures.

Chemical pesticides include organophosphate pesticides that affect the nervous system by disrupting the enzyme that regulates acetylcholine, a neurotransmitter. Most organophosphates are insecticides. They were developed during the early 19th century, but their effects on insects, which are similar to their effects on humans, were discovered in 1932. Some are very poisonous (they were used in World War II as nerve agents). However, they usually are not persistent in the environment.

Carbamate pesticides affect the nervous system by disrupting an enzyme that regulates acetylcholine, a neurotransmitter. The enzyme effects are usually reversible. There are several subgroups within the carbamates. Organochlorine Insecticides were commonly used in the past, but many have been removed from the market due to their health and environmental effects and their persistence (e.g. DDT and chlordane). Pyrethroid Pesticides were developed as a synthetic version of the naturally occurring pesticide pyrethrin, which is found in chrysanthemums. They have been modified to increase their stability in the environment. Some synthetic pyrethroids are toxic to the nervous system.

Biopesticides, for example, biochemical pesticides, are certain types of pesticides derived from such natural materials as animals, plants, bacteria, and certain minerals. As one example, canola oil and baking soda have pesticidal applications and are considered biopesticides. At the end of 2001, in the U.S. there were approximately 195 registered biopesticide active ingredients being used in 780 products. The following are three primary types of biopesticides:

Microbial pesticides consist of a microorganism (e.g., a bacterium, fungus, virus or protozoan) as the active ingredient. Microbial pesticides can control many different kinds of pests, although each separate active ingredient is relatively specific for its target pest[s]. For example, there are fungi that control certain weeds, and other fungi that kill specific insects. The most widely used microbial pesticides are subspecies and strains of *Bacillus thuringiensis*, or Bt. Each strain of this bacterium produces a different mix of proteins, and specifically kills one or a few related species of insect larvae. While some Bt's control moth larvae found on plants, other Bt's are specific for larvae of flies and mosquitoes. The target insect species are determined by whether the particular Bt produces a protein that can bind to a larval gut receptor, thereby causing the insect larvae to starve.

Plant-Incorporated-Protectants (PIPs) are pesticidal substances that plants produce from genetic material that has been added to the plant. For example, scientists can take the gene for the Bt pesticidal protein, and introduce the gene into the plant's own genetic material. Then the plant, instead of the Bt bacterium, manufactures the substance that destroys the pest. The protein and its genetic material, but not the plant itself, are regulated by EPA.

Biochemical pesticides are naturally occurring substances that control pests by non-toxic mechanisms. Conventional pesticides, by contrast, are generally synthetic materials that directly kill or inactivate the pest. Biochemical pesticides include substances, such as insect sex pheromones that interfere with mating as well as various scented plant extracts that attract insect pests to traps. Because it is sometimes difficult to determine whether a substance meets the criteria for classification as a biochemical pesticide, EPA has established a special committee to make such determinations.

I. Plant Extracts

In some embodiments, the present invention provides plant extracts with biopesticide activity. The plant extracts of the present invention demonstrate biopesticide activity against a variety of pests, including, but not limited to, Colorado potato beetle and leafrollers.

The present invention is not limited to a particular plant for use in preparing extracts. Exemplary plants include, but are not limited to, Apiaceae family (e.g., *Bifora radians, Conium maculatum*); Apocynaceae family (e.g., *Nerium oleander*); Araliaceae family (e.g., *Hedera helix*); Asteraceae family (e.g., *Arctium lappa, Xanthium strumarium, Artemisia vulgaris, Chrysanthemum segetum, Circium arvense*); Canabinaceae family (e.g., *Humulus lupulus*); Caprifoliaceae family (e.g., *Sambucus nigra*); Chenopodiaceae family (e.g., *Chenopodium album*); Cucurbitaceae family (e.g., *Ecballium elaterium*); Fabaceae family (e.g., *Glycyrrhiza glabra*); Guttiferae family (e.g., *Hypericum perforatum*); Lamiaceae family (e.g., *Salvia officinalis*); Lauraceae family (e.g., *Laurus nobilis*); Poaceae family (e.g., *Avena sterilis, Cynodon dactylon, Lolium temulentum, Sorghum halepense*); Ranunculaceae family (e.g., *Delphinium consolida*); Resedaceae family (e.g., *Reseda lutea*); Rubiaceae family (e.g., *Galium aperina*); Rubiaceae family (e.g., *Rubia tinctoria*); Scrophylaceae family (e.g., *Verbascum* spp such as *Verbascum songaricum*); Solanaceae family (e.g., *Datura stramonium; Solanum nigrum*); Styracaceae family (e.g., *Styrax officinalis*); and Urticaceae family (e.g., *Urtica dioica*). Particularly preferred plants include *A. vulgaris, A. lappa, H. helix, H. lupulus, L. temulentum, R. tinctoria, S. officinalis, S. nigra, U. dioica, Verbascum*_spp., *X. strumarium, C. album, R. lutea, S. nigrum, Bifora radians, A. lappa,* and *C. maculatum.*

The present invention is not limited to the plants disclosed herein. Additional plant extracts are generated and analyzed for biopesticide activity using, for example, the methods described in the Experimental section below.

In some embodiments, plant samples are dried (e.g. at room temperature in the dark). Samples are then ground in a mill. Samples are then extracted with a solvent (e.g., methanol). In some embodiments, samples are then filtered and dried. The resulting residue is dissolved in a solvent (e.g., water or water and acetone) to yield a final suspension. In some embodiments, suspensions are generated with different concentrations of plant material. In some embodiments, the extract preparation methods described in Examples 1-3 below are utilized.

In some embodiments, active ingredients (e.g., with biopesticide activity) are further purified. Purification methods are well known in the art and include, but are not limited to, extraction, fractionation, and chromatography. The presence of active ingredient is followed at each step of the process (e.g., using the activity assays described herein) and fractions with active ingredients are carried to the next step.

In some embodiments, purified active components are identified. Methods for identifying both small molecule and large molecule (e.g., protein) components are well known in the art and include, but are not limited to, spectroscopy (e.g., mass spectrometry), and nuclear magnetic resonance.

II. Plants

The methods of the present invention find use in the protection of a variety of plants of interest from pests. The present invention is not limited to a particular plant. The methods and compositions of the present invention are suitable for protecting any plant against pests. In some preferred embodiments, the methods and compositions of the present invention find use in the protection of crop plants against pests. Crop plants include any plant grown for commercial, industrial or food use. Examples include, but are not limited to, food for human consumption (e.g., grains, vegetables, fruits), food for consumption by animals (e.g., animals intended for consumption by humans), crops for industrial use (e.g., generation of industrial oils), etc. In, some preferred embodiments, the compositions of the present invention find use in the protection of pome fruits (e.g., apples) and potatoes against pests.

The present invention is not limited to use on crop or commercial plants. In some embodiments, plant extracts are utilized to control pests on home gardens or house plants. In other embodiments, plant extracts are utilized to control pests on commercial or home grown ornamental plants.

III. BioPesticides

As described above, the plant extracts of the present invention find use in the prevention of pest damage to plants of interest. The extracts of the present invention are active against a variety of common pests.

A. Pests

In some embodiments, the present invention provides methods of protecting plants against pests. In some embodiments, plant extracts of the present invention are used to protect plants against Colorado potato beetle or leafrollers. The present invention is not limited to use against the pests described herein. Extracts may be assayed using known methods (e.g., those disclosed herein) to determine their efficacy against additional insects and other pests.

The present invention is not limited to a particular application method. Plant extracts of varied strengths may be applied to plants of interest using any suitable method. In some embodiments, liquid extracts are sprayed or misted onto plants. For large scale application, aerial application is a desired method. In some embodiments involving small scale application, hand held sprayers are utilized. In other embodiments, extracts are lyophilized or powdered and a plant extract powder is sprayed or dusted onto plants. In yet other embodiments, plant extract products are applied as granules.

Plant extracts are applied as needed for pest control in one or more applications. In some embodiments, plant extracts are applied before detection of pests. In other embodiments, plant extracts are applied at the first sign of appearance of a pest (e.g., larvae or adult stage) and application is continued until all signs of the pest are removed. In yet other embodiments, plant extracts are applied at regular intervals throughout the growing season.

B. Combination Applications

In some embodiments, the present invention provides combination methods for controlling pests. The present invention is not limited to a particular mechanism. Indeed, an understanding of the mechanism is not necessary to practice the present invention. Nonetheless, it is contemplated that plant extracts of the present invention find use in prolonging the useful activity of traditional pesticides (e.g., by delay the development of resistance or allowing for lower dosages).

For example, in some embodiments, plant extracts of the present invention are applied in combination with know pesticides (e.g., commercially available chemical, biological or biopesticides). In some embodiments, combination solutions that comprise both a plant extract of the present invention and a known pesticide are generated and applied to plants. In other embodiments, known pesticides are applied separately from plant extracts of the present invention. In some embodiments, application of a plant extract of the present invention and a known pesticide are alternated. In other embodiments, plant extracts and known pesticides are applied at different points in the growing cycle of a plant.

C. Additional Applications

The present invention is not limited to the applications described above. In some further embodiments, the plant extracts of the present invention are utilized as attractants in aerosols and bait-traps (e.g., against household pests such as mosquitoes and cockroaches). In such embodiments, an extract of the present invention is combined with a known pesticide or insecticide in a trap or other delivery vehicle. The plant extracts of the present invention attract pests, which are then killed by a combination of the plant extract and/or the known insecticide.

In yet other embodiments, the compositions of the present invention are utilized as a protectant in stored products (e.g., textiles, food products, etc.). One skilled in the relevant arts knows how to apply the compositions and methods of the present invention to additional applications.

EXPERIMENTAL

The following examples are provided in order to demonstrate and further illustrate certain preferred embodiments and aspects of the present invention and are not to be construed as limiting the scope thereof.

Example 1

Materials and Methods

Insects

Obliquebanded leafrollers were drawn from a 4-yr laboratory colony originally collected as $1^{st}$ and $2^{nd}$ generation pupae from apple orchards in southwestern Michigan. Redbanded leafrollers came from a long-established laboratory colony maintained at Geneva, N.Y. by W. Roelofs. Moths were reared at 24° C. on pinto bean diet under a 16:8 (L:D) photoperiod. Male and female pupae of each species were segregated in 1 L plastic cages containing a 5% sucrose solution in plastic cups with dental cotton wick protruding from their lids. After emergence, moths were incubated for 24 hr at above-described conditions and subsequently transferred into 1-liter cups.

Plant Extracts

Five natural-product sources were used per study. The plants (Table 1) were all collected from sandy lime soil during spring and summer of 2002 in Taçliçiftlik, Tokat, in a temperate region of Turkey, where the altitude is 600 m. Samples were dried at room temperature for 3 wk in the dark and subsequently were ground in a mill (M 20 IKA Universal Mill, IKA Group). Ground plants were stored in 2000-ml glass jars at 18±2° C. in the dark. Fifty-gram samples were placed into 1000-ml Erlenmeyer flasks with 500-ml of methanol (Sigma). Flasks were covered with aluminum foil, placed on a horizontal shaker (HS 260 Basic, IKA Group) and shaken (120 oscillations/min for 24 h) in the dark. The suspension was filtered through two layers of cheese cloth, transferred into a 250-ml evaporating flask and dried in a rotary evaporator (RV 05 Basic 1B, IKA Group) at 32±2° C. The resulting residue was weighed and mixed with acetone to yield a 20% (w/w) plant suspension.

Electroantennograms

The EAG system and test protocols have been detailed by Stelinski et al. (2003 J. Chem. Ecol. 29: 403-422; Physiol. Entomol. 28: 97-107). Two milligrams of plant extracts (Table 1) or pheromone ((Z)11-14:Ac (lot #10010), Shin Etsu Tokyo, Japan) were diluted in acetone (20 µl total solution) and pipetted onto 1.4×0.5 cm strips of Whatman No. 1 filter paper. After 5 min in a fume hood for solvent evaporation, treated strips were inserted into disposable glass Pasteur pipettes. EAGs were measured as the maximum amplitude of depolarization elicited by 1-ml puffs of air through EAG-cartridges directed over live-insect preparations.

Male and female obliquebanded leafrollers and redbanded leafrollers were 2-4 d old when used for electroantennograms. Insects were restrained on a wax-filled, 3.5 cm diameter Petri dish by placing clay (10×3 mm) over their thorax and abdomen. The terminal 2 segments of the antenna destined for recording were removed with fine scissors and the recording electrode was placed over the severed end. The reference electrode was inserted into the neck. For each sample tested, EAGs were recorded from ten moths of each sex. Control stimulations (using filter paper impregnated with 20 µl of acetone solvent) were "puffed" before and after each stimulus presentation. Two puffs of each volatile treatment and control spaced 12 sec apart were administered to yield duplicate depolarization amplitudes for each replicate moth. The experiment was conducted in a randomized complete block design with chemical and moth sex as factors. Ten replicates were conducted for each moth sex and species combination.

Olfactometer Study

Male or female obliquebanded leafrollers used in this study were 1-3 d old. They were reared as described above. Discs, 55 mm in diameter, were cut from the sticky liners of pheromone traps (LPD Scenturion Guardpost, Suterra, Bend, Oreg.) intended for catching Lepidoptera. Each sticky disc was cleaned with acetone and placed into sterile 90-mm disposable Petri dish. Twenty millimeter diameter discs, cut from Whatman Number 1 filter paper, were placed centrally on top of the 55-mm sticky discs. Twenty-five microliters of each plant extract, diluted in acetone (20% w/w), was applied to the central filter paper disc. In the control treatment, 25-µl of acetone was applied to the disc. In the positive control, 25-µl of the pheromone component (Z)11-14:Ac was applied. In addition to positive control and negative or non-treatment control discs, a three-component obliquebanded leafroller pheromone in a rubber septum was also used as a standard. The septa were loaded with 0.485 mg of (Z)- and 0.015 mg (E)-11-tetradecenyl acetates and 0.026 mg of (Z)-11-tetradecenol (Hill and Roelofs 1979). After completing applications, the treated discs were left to dry in a fume hood for 15 min.

The treated discs and rubber septum with pheromone were transferred into an eight-arm wheel olfactometer using clean forceps (FIG. 1). The wheel olfactometer was connected to a vacuum pump set at 100 mm Hg, which suctioned air into the olfactometer through a hydrocarbon trap (Alltech Item No: 14633, Alltech Associates, Inc., IL). For each replicate, ten obliquebanded leafroller males or females were released into the central release point of the olfactometer. Each replicate was conducted at 24° C. and at a 16:8 light:dark photo regime. Counts of obliquebanded leafrollers in each olfactometer arm were made after 24 h. The experiment was conducted as a randomized complete block design with six replicates.

Antioviposition Study:

Experiments were conducted using plastic 1-liter bioassay cups 140 mm in height and 110 mm in diameter. Four windows (30×30 mm) were cut in each bioassay cup 90° apart around its circumference, 60 mm above its bottom. They were covered with fine mesh. Acetone-cleaned wax paper (50×100 mm) was attached to the interior wall of each bioassay cup. In the control treatment, 100-µl of acetone was applied to each side of wax paper and spread with a sterile bent glass rod "hockey stick". In each treatment, 100-µl of each acetone suspension of plant extract (20% w/w) was applied to each side of the wax paper and spread onto the wax paper with a sterile glass hockey stick. The wax papers were left to dry in a fume hood for 15 min. In choice bioassays, the cups contained one acetone-treated wax paper and one plant-extract-treated wax paper placed 30 mm from the edge of bioassay cups suspended by string from the top of the cup. A 5% sucrose solution was provided within bioassay cups. Five female and 3 male obliquebanded leafroller adults (one day post emergence) were transferred into each bioassay cup. The number of individual eggs within egg masses was counted and removed every 24 h for 7 days. Freshly treated wax paper was replaced daily. The experiment was replicated six times.

Data Analysis

Electroantennogram data were subjected to analysis of variance (ANOVA) and differences in pairs of means between treatments were separated using Tukey's multiple comparisons test (SAS Institute 2000).

For the olfactometer test, the number of male insects attracted by each treatment was expressed as a percentage of the total number of insects tested in each replicate. The resulting preference values for the treatments totaled 100%. The data were normalized using arcsine transformation. The transformed data were analyzed using single-factor ANOVA (Minitab Release 14) (P=0.05) followed by Tukey's test (P=0.05). Two-sample t-tests (Minitab Release 14) were performed to test effects of sex on attractiveness of plant extracts and pheromone.

For the oviposition choice test, egg counts were presented as a percentage. Within replicates, the cumulative number of eggs laid on each treatment was divided by the total number of eggs laid on each treatment. Therefore, the resulting preference values for the treatments totaled 100%. The data were normalized using arcsine transformation and then were subjected to paired t-tests (P=0.05) (Minitab Release 14).

Results

Electroantennogram Studies—Obliquebanded Leafroller

The EAG responses of male obliquebanded leafrollers were significantly (F=12.7, df=1, 63, P<0.01) higher than those of females for each treatment except for the control and H. lupulus. The highest EAG responses to a plant extract recorded from male obliquebanded leafrollers were to X. strumarium; these were significantly (F=8.5, df=9, 63, P<0.01) higher than those recorded for H. lupulus (Table 2). The EAG responses of male obliquebanded leafrollers to all of the plant extracts were significantly (F=8.5, df=9, 63, P<0.01) higher than that to the control (Table 2).

The EAG responses of female obliquebanded leafrollers to all of the plant extracts tested were significantly (F=17.6, df=9, 63, P<0.01) higher compared with the control (Table 2). The highest EAG responses from female obliquebanded leafrollers were recorded for B. radians and X. strumarium;

these responses were significantly (F=17.6, df=9, 63, P<0.01) higher compared with *H. lupulus, A. lappa*, and *Verbascum* spp (Table 2).

Electroantennogram Studies—Redbanded Leafroller

The responses of male redbanded leafrollers were significantly (F=18.5, df=1, 63, P<0.01) higher compared with females for each treatment except for the control and *H. lupulus*. The EAG responses of male redbanded leafrollers to pheromone were significantly (F=7.2 df=9, 63, P<0.01) higher compared with all of the plant extracts tested (Table 3). *X. strumarium* elicited significantly (F=7.2 df=9, 63, P<0.01) higher EAG responses from male redbanded leafrollers compared with all of the other plant extracts tested (Table 3). The responses of female redbanded leafrollers to all of the plant extracts tested were significantly (F=13.0, df=9, 63, P<0.01) higher than the control; but did not differ significantly (F=0.5, df=9, 63, P>0.1) among themselves (Table 3).

Olfactometer Studies—Obliquebanded Leafroller

There was a significant treatment effect of the plant extracts tested on the behavior of obliquebanded leafroller males (F=7.61, df=7, 47, P<0.001). *X. strumarium* appeared to be the most attractive extract capturing an average 24.3% of the insects released. Significantly more male obliquebanded leafrollers were attracted to *X. strumarium* than to pheromone on paper, *H. lupulus, Verbascum* spp., or the control (Table 4). Compared with the control, there was no significant attraction to pheromone on filter paper, *A. lappa, H. lupulus*, and *Verbascum* spp. There was no significant difference in percent attraction among pheromone in septum, *A. lappa, B. radians*, and *X. strumarium* (Table 4).

The percentage of female obliquebanded leafrollers captured varied from 2.6% (*H. lupulus*) to 29.7% (*X. strumarium*) and only *X. strumarium* was significantly different from the control (F=5.31, df=7, 47, P<0.01). There were no significant differences in the numbers of female obliquebanded leafrollers attracted to *B. radians, A. lappa, H. lupulus* and *Verbascum* spp; however, significantly more females were attracted to *X. strumarium* than to *H. lupulus*.

The behavioral responses of female obliquebanded leafrollers to the plant extracts were similar to that of males, except in the case of *Verbascum* spp. (Table 4). *Verbascum* spp. extracts captured significantly more females than males. Although more females than males were attracted to *X. strumarium*, this was not significant (t=−1.23, df=10, P>0.1). Significantly (t=2.30, df=10, P<0.05) more males were attracted to pheromone in septa compared with females. Pheromone on paper and in septa did not attract female obliquebanded leafrollers; 1.1 and 5.3% responded, respectively, and these values did not differ significantly (P>0.05) from the control.

Antioviposition Experiment—Obliquebanded Leafroller Females

Figure 2:
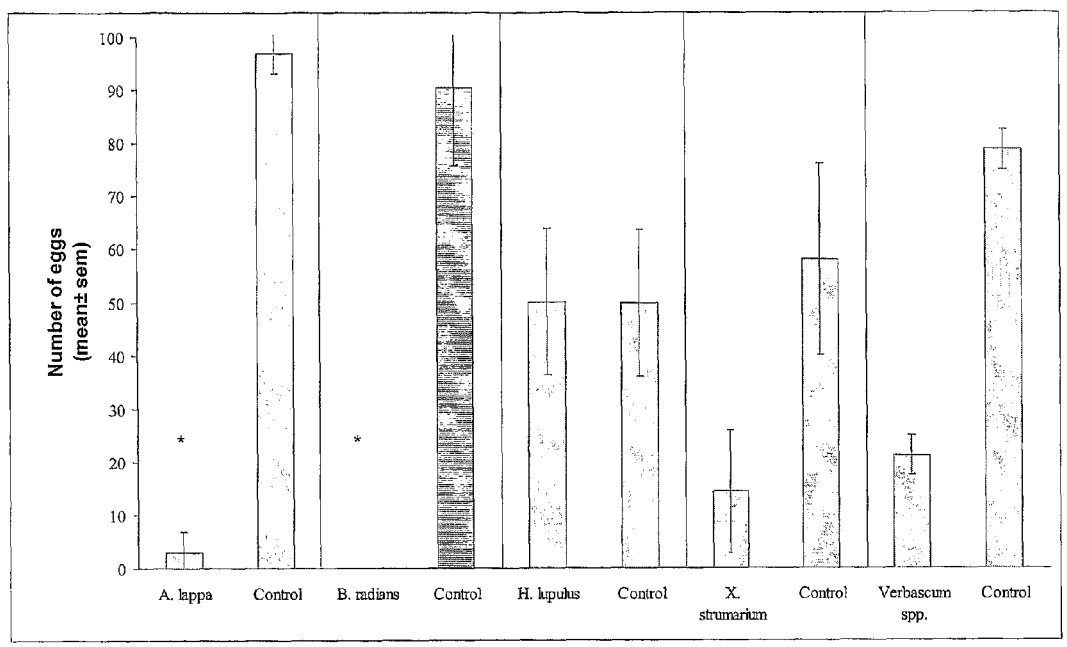
FIG. 2 shows the number of eggs oviposited by female obliquebanded leafrollers, *Choristoneura rosaceana*, in choice tests comparing various plant extracts with solvent controls.

Female obliquebanded leafrollers started to lay eggs 1-2 days after adult emergence and continued for up to 7 days. The oviposition behavior of obliquebanded leafroller females was significantly affected by the plant extract suspensions (FIG. 2). Among the tested plant extracts, *B. radians* induced the greatest anti-oviposition effect given that females did not lay any eggs on *B. radians*-treated wax paper. The total number of eggs laid by females on *A. lappa*-treated wax paper was also significantly lower compared with that on the controls. Although *X. strumarium* and *Verbascum* spp. reduced the number of eggs oviposited by ca. threefold, neither difference was statistically significant (t=−11.06, df=5, P>0.1, t=2.35, df=5, P>0.1). Females laid as many eggs on *H. lupulus*-treated wax papers as on the controls.

TABLE 1

Plants used in EAG, olfactometer, and oviposition studies.

| Family Name | Scientific name | Tissue used |
|---|---|---|
| Apiaceae | *Bifora radians* | Whole Plant |
| Asteraceae | *Arctium lappa* | Whole plant |
| Asteraceae | *Xanthium strumarium* | Fruit |
| Canabinaceae | *Humulus lupulus* | Flower bud |
| Scrophulariaceae | *Verbascum* spp | Whole plant |

TABLE 2

EAG responses of male and female obliquebanded leafrollers to various plant extracts and pheromone.

| | EAG responses (mV ± SE)[1] upon stimulation with 1 ml of air through stimulus cartridge | | |
|---|---|---|---|
| Treatment | Males | | Females |
| Control | 0.48 ± 0.06 d | NS | 0.16 ± 0.02 c |
| Pheromone | 4.87 ± 0.32 a | * | 0.45 ± 0.06 ab |
| *B. radians* | 1.36 ± 0.10 bc | * | 0.56 ± 0.06 a |
| *X. strumarium* | 2.25 ± 0.19 b | * | 0.61 ± 0.08 a |
| *H. lupulus* | 0.94 ± 0.10 c | NS | 0.47 ± 0.05 b |
| *A. lappa* | 1.36 ± 0.11 bc | * | 0.35 ± 0.05 b |
| *Verbascum* spp. | 1.24 ± 0.11 bc | * | 0.32 ± 0.04 b |

[1]Means within columns followed by the same letter are not significantly different (P = 0.01, Tukey's multiple comparisons test). Paired values within rows marked with an asterisk are significantly different (P < 0.01) whereas those marked NS are not.

TABLE 3

EAG responses of male and female redbanded leafrollers to various plant extracts and pheromone.

| | EAG responses (mV ± SE)[1] upon stimulation with 1 ml of air through stimulus cartridge | | |
|---|---|---|---|
| Treatment | Males | | Females |
| Control | 0.36 ± 0.07 d | NS | 0.14 ± 0.02 b |
| Pheromone | 5.42 ± 0.40 a | * | 0.43 ± 0.06 a |
| *B. radians* | 1.44 ± 0.05 c | * | 0.47 ± 0.08 a |
| *X. strumarium* | 2.26 ± 0.20 b | * | 0.49 ± 0.08 a |
| *H. lupulus* | 0.96 ± 0.09 c | NS | 0.52 ± 0.05 a |
| *A. lappa* | 1.54 ± 0.04 c | * | 0.44 ± 0.04 a |
| *Verbascum* spp. | 1.26 ± 0.09 c | * | 0.43 ± 0.06 a |

[1]Means within columns followed by the same letter are not significantly different (P = 0.01, Tukey's multiple comparisons test). Paired values within rows marked with an asterisk are significantly different (P < 0.01) whereas those marked NS are not.

TABLE 4

Behavioral responses of male and female obliquebanded leafrollers to various plant extracts and pheromone.

| | Attraction (Mean ± SEM)% | | |
|---|---|---|---|
| Treatment | Males | | Females |
| Control | 0.80 ± 0.80 c | NS | 1.14 ± 1.12 b |
| Pheromone on paper | 4.05 ± 1.66 bc | NS | 1.14 ± 1.12 b |
| Pheromone mixture in septum | 20.16 ± 0.07 ab | * | 5.28 ± 2.58 b |
| *B. radians* | 18.49 ± 0.64 ab | NS | 10.79 ± 1.53 ab |
| *X. strumarium* | 24.32 ± 0.50 a | NS | 29.67 ± 0.40 a |
| *H. lupulus* | 1.64 ± 0.97 c | NS | 2.57 ± 1.25 b |
| *A. lappa* | 11.74 ± 1.12 abc | NS | 11.06 ± 1.31 ab |
| *Verbascum* spp. | 4.46 ± 1.56 bc | * | 14.04 ± 0.47 ab |

[1]Means within columns followed by the same letter are not significantly different (P = 0.01, Tukey's multiple comparisons test). Paired values within rows marked with an asterisk are significantly different (P < 0.01) whereas those marked NS are not.

Example 2

Materials and Methods

Insects:

Colorado potato beetles were continuously reared on potato plants (*Solanum tuberosum* L. cultivar Morfana) at Gaziosmanpaşa University Research Station in Taşliçiftlik, Tokat. The field was designated for organic potato production and there was no pesticide application for 3 years prior to the initiation of this project. The field was divided into three different plots separated by maize barriers. Planting occurred at 2 wk intervals from April to June providing sufficient beetle stocks throughout the studies. Adult insects from a panmictic population collected throughout the region were released into successive plots when potato plants were in the four or the five leaflet stage. Third instar larvae were hand collected from the field prior to the experiments and segregated from other instars using a delimiter of 1.4-1.8 mm head capsule width measurement.

Plants and Sample Preparation

Thirty natural product sources were used per study. The plants (Table 5) were all collected during spring and summer of 2002 in Taşliçiftlik, Tokat, in temperate region of Turkey, where the attitude is 600 m and the soil is sandy lime soil, except *Styrax officinalis* L. and *H. helix*, which were obtained from Mersin. Samples were dried at room temperature for three weeks in the dark and subsequently were ground in a mill (M 20 IKA Universal Mill, IKA Group). Ground plants were stored in 2000 ml glass jars at 18±2° C. in the dark.

Fifty grams of sample were placed into 1000 ml Erlemneyer flasks with 500 ml of methanol (Sigma). Flasks were covered with aluminum foil, placed on a horizontal shaker (HS 260 Basic, IKA Group) and shaken (120 oscillations/min for 24 h) in the dark. The suspension was filtered through two layers of cheese cloth, transferred into a 250 ml evaporating flask and excess methanol evaporated in a rotary evaporator (RV 05 Basic 1B, IKA Group) at 32±2° C. The resulting residue was weighted and eluted with sufficient distilled water containing 10% acetone (w/w) to yield a 40% (w/w) plant suspension.

Bioassay Contact Effects

Preliminary bioassays demonstrated that 2 ml of plant residue suspensions produced reproducible results; therefore, 2 ml of each plant extract was applied to 20 $3^{rd}$ instar larvae using the Potter Spray Tower set at 10 PSI and equipped with a nozzle of 0.7 mm internal diameter. Two ml of the distilled water containing 10% acetone was also applied to 20 larvae in each replicate as a negative control along with imidacloprid (CONFIDOR SL, Bayer) at manufacturer recommended rate as a positive control. After spraying, the larvae were transferred into 1000 ml glass jars and provided with fresh potato leaflets. The top of each jar was covered with cheese cloth and held at 28±2° C. and 16 h: 8 h light dark photo regime. Mortalities were recorded at 24 h intervals for 7 days. A randomized complete block design was used in this study. Each treatment was replicated three times within a trial and each trial was repeated three times.

Residual Effects

Stomach poison effects of the thirty plant extracts were assed by morbidity assays using $3^{rd}$ instar larvae fed on treated potato leaflets. Preliminary assays demonstrated that 20% (w/w) plant extracts in distilled water containing 10% acetone did not produce phytotoxicity and were easily and uniformly applied to leaflets.

Leaflets were treated with 2 ml of each plant extract suspension in distilled water containing 10% acetone with the Potter Spray Tower set at 10 PSI with a 0.7 mm internal diameter nozzle. After treatment, the leaflets were dried at room temperature for about 5 min. The cut end of each leaflet petiole was covered with a 30×55 mm piece of sterile cotton wool, which was moistened with 2 ml of water containing 1% NPK (20-20-20) fertilizer. This treatment ensured that the excised leaflet remained green for at least 7 days. Treated leaflets were transferred into 1000 ml glass jars to which 20 $3^{rd}$ instar larvae were added before incubation as described above. Mortalities were assessed at 24 hr intervals for 7 days. Control leaflets were treated with 2 ml of distilled water containing 10% acetone and the standard imidacloprid control was used as described above. Each treatment was repeated three times per block and blocks were completed in a randomized complete block design.

Data Analysis

Data were corrected for mortality in the controls using Abbotts formula and then normalized using arcsine transformation. Transformed data were analyzed using ANOVA ($\alpha=0.05$) and Tukeys mean separation ($\alpha=0.05$). Incubation time effects were assed using a one-tailed paired-sample t-test ($\alpha=0.05$). All statistical analyses were carried out using MINITAB computer software Release 14.

Results

Contact Effects

The experimental protocol, which involved limited handling, spraying and incubation did not appear deleterious to beetle larvae because few controls succumbed during any 8 d of the studies (Table 6). The mortality induced by the crude plant extracts after 24 hr of incubation varied from 0 to 91% and mortality from *A. vulgaris, H. helix, H. lupulus, L. temulentum, R. tinctoria, S. officinalis, S. nigra, U. dioica, Verbascum* spp. and *X. strumarium* crude extracts were significantly higher than the control (F=50.08, df=31, 64, P<0.005). Fifteen of the crude plant extracts did not cause beetle mortality from which *Conium maculatum* L., *C. album, S. officinalis, Galium aperina* L., and *Sorghum halepense* (L.) Pers. were the least toxic (Table 6). After 24 h of incubation, the most toxic extract was from *H. lupulus*, which caused 91% mortality. For most crude plant extracts, increasing incubation time from 24-48 h did not cause a significant difference in mortality, but an increase was seen for *Nerium oleander* L., *Arctium lappa* L., *X. strumarium, C. album, Cynadon dactylon* L., *L. temulentum, Verbascum* spp. and *Datura stramonium* L. extracts (Table 6). The most dramatic increase in the 24-48 h was seen from *C. album* crude extract where toxicity increased from 1% to 26%.

After 48 h of incubation mortality varied significantly between the tested extracts and twelve inflicted significant mortality (F=39.05, df=31, 64, P<0.000). *H. lupulus* extract yielded 99% mortality after 48 hr which is similar to mortality caused by imidacloprid. However, only 1% was recorded from *C. maculatum, Glycyrrhiza glabra* L., *Avena sterilis* L. and *Delphinium consolida* L. extracts. Five plant extracts, *Circium arvense* (L.) Scop., *Ecballium elaterium* (L.) A. Rich., *Hypericum perforatum* L., *Laurus nobilis* L. and *S. nigrum*, did not cause any mortality after 48 hr and *A. vulgaris, X. strumarium, S. nigra, C. album* and *R. tinctoria* showed moderate mortality (Table 6).

Residual Effects

Twenty crude plant extracts caused some increase in mortality as compared to the control values after 48 h incubation (Table 7). Mortality varied from 0.6% (*H. helix, A. lappa, A. vulgaris, H. perforatum, S. officinalis* and *U. dioica*) to 20.9% (*H. lupulus*) and only *H. lupulus, L. temulentum, R. lutea* and *S. nigrum* were significantly different from the control (F=7.38, df=31.64, P<0.000). Imidacloprid provided 71.9% mortality. Increasing incubation time from 48-72 h did not cause any significant increase in mortalities except from *C. maculatum* and *C. album* extracts (Table 7). These data indicated that 48 h of incubation was usually sufficient to assess the residual toxicity potential.

After 72 h, all plant extracts, except *L. nobilis* and *E. elaterium*, appeared to exhibit some lethality to the $3^{rd}$ instar larvae but overall significant variation occurred between plant extracts (F=6.28, df=31.64, P<0.000). *R. tinctoria* killed 0.6% of larvae, whereas an intermediate level of toxicities was demonstrated by *H. lupulus, L. temulentum, R. lutea* and *S. nigrum* resulting in mortalities of 22.5, 24.0, 22.5 and 26.2% respectively. *C. album* was the most toxic extract, killing 34.9% of exposed larvae.

Residual effects of crude plants extracts to $3^{rd}$ instar larvae were far less pronounced when compared with their contact toxicities. Leaflets treated with *Bifora radians* M. Bieb., *A. lappa, X. strumarium, Verbascum* spp. and *C. maculatum* extracts exhibited antifeedant effects as leaflets were only partly consumed by the larvae and this resulted in low mortalities but little foliage damage.

TABLE 5

Plants used in contact and residual toxicity bioassay on Colorado potato beetle

| Family Name | Scientific name | Tissue used |
| --- | --- | --- |
| Apiaceae | *Bifora radians* | Whole Plant |
| Apiaceae | *Conium maculatum* | Whole Plant |
| Apocynaceae | *Nerium oleander* | Flowers |
| Araliaceae | *Hedera helix* | Leaves |
| Asteraceae | *Arctium lappa* | Whole plant |
| Asteraceae | *Artemisia vulgaris* | Leaves |
| Asteraceae | *Chrysanthemum segetum* | Whole plant |
| Asteraceae | *Circium arvense* | Whole plant |
| Asteraceae | *Xanthium strumarium* | Fruit |
| Canabinaceae | *Humulus lupulus* | Flower bud |
| Caprifoliaceae | *Sambucus nigra* | Fruit |
| Chenopodiaceae | *Chenopodium album* | Whole plant |
| Cucurbitaceae | *Ecballium elaterium* | Fruit |
| Fabaceae | *Glycyrrhiza glabra* | Fruit |
| Guttiferae | *Hypericum perforatum* | Whole plant |
| Lamiaceae | *Salvia officinalis* | Whole plant |
| Lauraceae | *Laurus nobilis* | Leaves |
| Poaceae | *Avena sterilis* | Whole plant |
| Poaceae | *Cynodon dactylon* | Whole plant |
| Poaceae | *Lolium temulentum* | Whole plant |
| Poaceae | *Sorghum halepense* | Fruit |
| Ranunculaceae | *Delphinium consolida* | Whole plant |
| Resedaceae | *Reseda lutea* | Fruit |
| Rubiaceae | *Galium aperina* | Whole plant |
| Rubiaceae | *Rubia tinctoria* | Fruit |
| Scrophyllaceae | *Verbascum* spp | Whole plant |
| Solanaceae | *Datura stramonium* | Fruit |
| Solanaceae | *Solanum nigrum* | Fruit |
| Styracaceae | *Styrax officinalis* | Fruit |
| Urticaceae | *Urtica dioica* | Whole plant |

TABLE 6

Mortality % (mean ± SEM) caused by contact effect of plant extracts to 3 rd instar Colorado potato beetle larvae after 24 and 48 h incubation at 28 ± 2° C.

| Treatment | 24 h | 48 h |
| --- | --- | --- |
| *Bifora radians* | 0.00 ± 0.00 e*A | 3.29 ± 0.90 cd A |
| *Conium maculatum* | 0.56 ± 0.56 de A | 1.15 ± 1.14 d A |
| *Nerium oleander* | 0.00 ± 0.00 e A | 5.00 ± 0.00 cd B |
| *Hedera helix.* | 11.57 ± 0.06 c A | 13.01 ± 0.22 c A |
| *Arctium lappa* | 0.00 ± 0.00 e A | 8.16 ± 0.10 cd B |
| *Artemisia vulgaris* | 23.29 ± 0.04 c A | 24.89 ± 0.14 bc A |
| *Chrysanthemum segetum* | 0.00 ± 0.00 e A | 3.29 ± 0.90 cd A |
| *Circium arvense* | 0.00 ± 0.00 e A | 0.00 ± 0.00 d A |
| *Xanthium strumarium* | 26.44 ± 0.24 c A | 34.67 ± 0.65 b B |
| *Humulus lupulus* | 91.07 ± 3.89 b A | 99.44 ± 0.56 a A |
| *Sambucus nigra* | 24.89 ± 0.13 c A | 26.52 ± 0.15 bc A |
| *Chenopodium album* | 1.15 ± 1.13 de A | 26.44 ± 0.25 bc B |
| *Ecballium elaterium* | 0.00 ± 0.00 e A | 0.00 ± 0.00 d A |
| *Glycyrrhiza glabra* | 0.00 ± 0.00 e A | 0.56 ± 0.56 d A |
| *Hypericum perforatum* | 0.00 ± 0.00 e A | 0.00 ± 0.00 d A |
| *Salvia officinalis* | 19.84 ± 0.13 c A | 21.62 ± 0.04 bc A |
| *Laurus nobilis* | 0.00 ± 0.00 e A | 0.00 ± 0.00 d A |
| *Avena sterilis* | 0.00 ± 0.00 e A | 0.56 ± 0.56 d A |
| *Cynodon dactylon* | 0.00 ± 0.00 e A | 8.16 ± 0.11 cd B |
| *Lolium temulentum* | 14.76 ± 0.16 c A | 19.84 ± 0.13 bc B |
| *Sorghum halepense* | 0.56 ± 0.56 de A | 3.29 ± 0.90 cd A |
| *Delphinium consolida* | 0.00 ± 0.00 e A | 0.56 ± 0.56 d A |
| *Reseda lutea* | 0.00 ± 0.00 e A | 2.24 ± 0.56 d A |
| *Galium aperina* | 0.56 ± 0.56 de A | 2.24 ± 0.56 d A |
| *Rubia tinctoria* | 11.57 ± 0.06 c A | 23.29 ± 0.04 bc A |
| *Verbascum* spp | 13.24 ± 0.06 c A | 19.84 ± 0.13 bc B |
| *Datura stramonium* | 0.00 ± 0.00 e A | 9.60 ± 0.25 cd B |
| *Solanum nigrum* | 0.00 ± 0.00 e A | 0.00 ± 0.00 d A |
| *Styrax officinalis* | 0.56 ± 0.56 de A | 3.29 ± 0.90 cd A |
| *Urtica dioica* | 7.79 ± 0.33 cd A | 13.24 ± 0.06 c A |
| Imidacloprid | 100 ± 0.00 a A | 100 ± 0.00 a A |
| Control | 0.00 ± 0.00 e A | 0.56 ± 0.56 d A |

*Means in a column followed by a different lowercase letter are significantly different (P < 0.005, Anova, Tukey Test). Means in a row followed by a different uppercase letter are significantly different ((P < 0.005, Paired t-test)

TABLE 7

Residual toxicities % (mean ± SEM) of plant extracts to 3 rd instar Colorado potato beetle larvae after 48 and 72 h incubation at 28 ± 2° C.

| Treatment | 48 h | 72 h |
| --- | --- | --- |
| *Bifora radians* | 1.15 ± 1.13 bc* A | 1.75 ± 1.72 c A |
| *Conium maculatum* | 0.00 ± 0.00 c A | 5.00 ± 0.00 bc B |
| *Nerium oleander* | 0.00 ± 0.00 c A | 3.29 ± 0.90 bc A |
| *Hedera helix.* | 0.56 ± 0.56 bc A | 2.24 ± 0.56 bc A |
| *Arctium lappa* | 0.56 ± 0.56 bc A | 6.11 ± 2.24 bc A |
| *Artemisia vulgaris* | 0.56 ± 0.56 bc A | 4.25 ± 1.31 bc A |
| *Chrysanthemum segetum* | 0.56 ± 0.56 bc A | 4.53 ± 1.13 bc A |
| *Circium arvense* | 2.24 ± 0.56 bc A | 5.18 ± 1.76 bc A |
| *Xanthium strumarium* | 0.00 ± 0.00 c A | 2.24 ± 0.56 bc A |
| *Humulus lupulus* | 20.91 ± 0.61 b A | 22.46 ± 0.77 bc A |
| *Sambucus nigra* | 3.29 ± 0.90 bc A | 12.56 ± 0.50 bc A |
| *Chenopodium album* | 5.64 ± 1.46 bc A | 34.85 ± 0.27 b B |
| *Ecballium elaterium* | 0.00 ± 0.00 c A | 0.00 ± 0.00 c A |
| *Glycyrrhiza glabra* | 3.29 ± 0.90 bc A | 6.49 ± 0.11 bc A |
| *Hypericum perforatum* | 0.56 ± 0.56 bc A | 2.24 ± 0.56 bc A |
| *Salvia officinalis* | 1.75 ± 1.73 bc A | 18.12 ± 0.18 bc A |
| *Laurus nobilis* | 0.00 ± 0.00 c A | 0.00 ± 0.00 c A |
| *Avena sterilis* | 0.00 ± 0.00 c A | 2.24 ± 0.56 bc A |
| *Cynodon dactylon* | 0.00 ± 0.00 c A | 4.53 ± 1.13 bc A |
| *Lolium temulentum* | 12.21 ± 0.67 b A | 23.96 ± 0.92 b A |
| *Sorghum halepense* | 4.53 ± 1.14 bc A | 6.49 ± 0.11 bc A |
| *Delphinium consolida* | 3.29 ± 0.90 bc A | 9.60 ± 0.25 bc A |
| *Reseda lutea* | 14.76 ± 0.16 b A | 22.46 ± 0.77 bc A |
| *Galium aperina* | 3.29 ± 0.90 bc A | 6.49 ± 0.11 bc A |
| *Rubia tinctoria* | 0.00 ± 0.00 c A | 0.56 ± 0.56 c A |
| *Verbascum* spp | 1.15 ± 1.13 bc A | 6.87 ± 1.73 bc A |
| *Datura stramonium* | 1.75 ± 1.73 bc A | 2.37 ± 2.33 bc A |
| *Solanum nigrum* | 18.27 ± 0.05 b A | 26.15 ± 0.50 bc A |
| *Styrax officinalis* | 0.56 ± 0.56 bc A | 2.24 ± 0.56 bc A |
| *Urtica dioica* | 0.56 ± 0.56 bc A | 3.29 ± 0.90 bc A |
| Imidacloprid | 71.89 ± 0.25 a A | 83.64 ± 0.23 a A |
| Control | 0.00 ± 0.00 c A | 6.49 ± 0.11 bc B |

*Means in a column followed by a different lowercase letter are significantly different (P < 0.005, Anova, Tukey Test). Means in a row followed by a different uppercase letter are significantly different ((P < 0.005, Paired t-test)

Example 3

Materials and Methods

Insects:

Colorado potato beetle (CPB) were reared on potato plants (*Solanum tuboresum* L. cultivar Morfana) at Gaziosmanpa Şa University Research Station in Ta şli çiftlik, Tokat as described above. The larvae were hand collected from the field prior to the experiment and segregated using head capsule measurements of 0.6-0.7 mm, 0.9-1.1 mm, 1.4-1.8 mm, 2.0-2.4 mm for 1, 2, 3, and 4 instars respectively. The adults in the experiments were newly enclosed 1-3 days olds.

Plants and Sample Preparation

The plant samples were prepared according to the procedure described above. Nine extracts were used in this study. The plants (Table 8) were all collected during spring and summer of 2002. Samples were dried at room temperature and were ground for 5 min in a mill (M 20 IKA Universal Mill, IKA Group). Fifty grams of dried plant samples was treated with 500 ml of methanol 99.9% (Sigma) for 24 h and the suspension was filtered through two layers of cheese cloth before excess methanol was evaporated in a rotary evaporator (RV 05 Basic 1B, IKA Group) at $32\pm2°$ C. The resulting residue was eluted with sufficient distilled water containing 10% acetone (w/w) to yield a 40% (w/w) plant suspension. For the dose-mortality bioassay, *H. lupulus* extract stock suspension was prepared as described above, containing 50% (w/w) plant extract/water with 10% acetone, and diluted in distilled water containing 10% acetone (w/w) to produce solutions containing 2.5, 5, 10, 20 and 40% (w/w).

Plant Extract Effects on Various Life Stages of Colorado Potato Beetle

Extract contact effects were determined on $1^{st}$-$4^{th}$ instar larvae as well as adult beetles. Twenty individuals for each development stage were transferred to Whatman filter paper in 90 mm disposable Petri dishes. The plant extract suspensions were shaken for 1 min and 2 ml of extract suspension was applied to each batch using a Potter spray tower set at 10 PSI with a 0.7 mm diameter fine droplet spray nozzle. After spraying, the insects were left to dry for 10 min at room temperature before transferring into a 1l glass jar with fresh potato leaflets. The insects were incubated at $28\pm2°$ C. and 16:8 hr photophase. Controls were treated with 2 ml sterile distilled water containing 10% acetone. Imidacloprid (CONFIDOR SL, Bayer) was used as a standard control and three groups of 20 insects were treated with 2 ml of imidacloprid at the manufacturer's recommended rate (1.5 μl/ml) in distilled water. Mortalities were recorded at 24 h intervals for 7 d. Data were submitted to a randomized complete block statistical analysis. Three replicates of each developmental stage were sprayed with a plant extract suspension, three were used as control in each trial and three trials were performed each consisting of 3 treatment replicates.

Toxicity of *H. lupulus* Crude Extract on Various Stages of Colorado Potato Beetle The toxicity of *H. lupulus* extract was submitted to an additional assay based on its effects on 1-4 larval and adult stages of CPB. In each replicate twenty insects, 1-4 larvae or adults, were placed on Whatman filter paper in a 90 mm Petri dish. The dorsal surface of each insect was sprayed under the Potter spray tower as described above with 2 ml of *H. lupulus* suspension containing 2.5, 5, 10, 20 or 40% (w/w) plant material. After spraying insects were incubated as described above and mortalities assessed after 24 and 48 h. In the control 20 insects were treated with 2 ml water containing 10% (w/w) acetone. Each bioassay was repeated three times in a trial and three trials were completed for a total of 9 replicated per dose.

Data Analysis

Screening data were corrected for mortality in the controls using Abbott's formula (Abbott, J Econ Entomol 18:265-267 (1925)) and then normalised using an arcsine transformation. Transformed data were analyzed using ANOVA ($P\leq0.05$) and Tukeys mean separation ($P\leq0.05$). All statistical analyses were carried out using MINITAB Release 14. Colorado potato beetle mortality obtained from dose-mortality bioassay utilizing *H. lupulus* was corrected for control mortality using Abbott's formula (supra). The corrected mortality data were analyzed using POLO-PC to estimate $LC_{50}$, $LC_{90}$ and the regression line slopes. Homogeneity of the regression lines between various developmental stages were tested using the maximum likelihood approximation test ($P\leq0.05$).

Results

Effects of Plant Extract on Various Life Stages of Colorado Potato Beetle

The screening evaluation of crude plant extracts revealed that there were differences between toxicities of extracts at various life stages; 1-$3^{rd}$ instars were very susceptible to various extracts while $4^{th}$ instar larvae and adults were less affected. The standard, imidacloprid, was very toxic to $1^{st}$ instar larvae and exhibited 100% mortality in 48 h. Relatively low (<20%) mortality was observed from most extracts to $1^{st}$ instar larvae, except *H. lupulus*. Mortalities ranged from 3.29% (*C. album*) to 19.6% (*V. songaricum*) (Table 9 (FIG. 4)). Mortality caused by *H. lupulus* was significantly different from the control after 48 h (F=47.67, df=10, 32, $P\leq0.05$). CPB $2^{nd}$ larvae appeared to be more susceptible to plant extracts generally but morbidity was still low for 6 plants. *H. lupulus* (73.4%) was the most toxic extract, followed by *L. temulentum* (13.3%) and *S. officinalis* (13.3%) (F=47.32, df=10, 32, $P\leq0.05$). Imidacloprid exhibited 94.8% mortality to $2^{nd}$ instar larvae. In $3^{rd}$ instars all the plant extracts increased mortality over the control after 48 h incubation. Third instar larval mortality varied from 1% (*C. album*) to 83.8% (*H. lupulus*) and only *H. lupulus* was significantly different from the control (F=40.06, df=10, 32 $P\leq0.05$). Imidacloprid mortality was 100% at the end of 48 h incubation period. All extracts, except *C. album, L. temulentum* and *X. strumarium*, yielded significant mortality in the $4^{th}$ larvae after 48 h incubation (F=7.28, df=10, 32, $P\leq0.05$); ranging from 9.6% (*V. songaricum*) to 40.0% (*H. lupulus*). *H. lupulus* again yielded significantly increased mortality over the other five plant extracts. Imidacloprid was not as toxic to $4^{th}$ stage larvae yielding only 11.5% mortality. Both *A. vulgaris* and *C. album* yielded significant adult mortality after 48 h (F=6.03, df=10, 32, $P\leq0.05$). Among plant extracts, *A. vulgaris* (24.7%) exhibited the highest adult mortality and it was significantly more effective than other any plant extract, except *C. album* (Table 9 (FIG. 4)). Imidacloprid was moderately toxic to adult Colorado potato beetle yielding nearly two fold more mortality than the most toxic plant extract.

Toxicity of *H. Lupulus* Crude Extract on Various Stages of Colorado Potato Beetle During multiple dose assays with H. lupulus extract, $LC_{50}$ values varied with CPB developmental stage (Table 10). The highest $LC_{50}$ value was observed for the fourth instar larvae, followed by third instar. The first and second instar larvae had the lowest $LC_{50}$ values, 9.98% and 11.8% respectively, and these were significantly different from the other stages (Table 10). The fourth instars exhibited an intermediate response when compared to adults, which confirms life-stage mediated tolerance to the extracts (Table 10).

TABLE 8

Plant used screening study on various development stages of Colorado potato beetle

| Family Name | Scientific name | Tissue used |
|---|---|---|
| Araliaceae | Hedera helix | Leaves |
| Asteraceae | Artemisia vulgaris | Leaves |
| Asteraceae | Xanthium strumarium | Fruit |
| Canabinaceae | Humulus lupulus | Flower bud |
| Caprifoliaceae | Sambacus nigra | Fruit |
| Chenopodiaceae | Chenopodium album | Whole plant |
| Lamiaceae | Salvia officinalis | Whole plant |
| Poaceae | Lolium temulentum | Whole plant |
| Scrophyllaceae | Verbascum songaricum | Whole plant |

TABLE 10

Dose-mortality responses of different stages of *Leptinotarsa decemlineata* treated with *Humulus lupulus*
Values in the same column followed by the same letter are not significantly different ($P < 0.05$).

| Tested stage of *L. decemlineata* | Number of insects tested | $LC_{50}$ (%) | Fiducial Limits (%) | Slope ± SE | Intercept ± SE | $\chi2$ |
|---|---|---|---|---|---|---|
| First stage larvae | 900 | 9.98 | 8.49-11.64 | 1.29 ± 0.12 c | −1.28 ± 0.14 | 0.46 |
| Second stage larvae | 900 | 11.80 | 8.99-15.29 | 1.48 ± 0.13 c | −1.59 ± 0.15 | 5.08 |
| Third stage larvae | 900 | 17.19 | 16.17-19.45 | 2.69 ± 0.24 a | −3.36 ± 0.31 | 2.05 |
| Fourth stage larvae | 900 | 46.39 | 39.74-56.95 | 2.07 ± 0.24 b | −3.45 ± 0.33 | 1.84 |
| Adult | 900 | —* | —* | 1.21 ± 0.34 d | −3.06 ± 0.51 | 0.53 |

*The calculated value exceeded 100% (w/w) such that these values are not presented.

Example 4

Materials and Methods

Insect Material

*Leptinotarsa decemlineata* beetles were obtained from the Alampi Beneficial Insect Laboratory, New Jersey Department of Agriculture, Trenton, N.J., USA. The insects were reared on potato plants, *Solanum tuberosum* L. cultivar Superior at 26±1° C., 45% RH and 16:8 L:D photoperiod regime. The colony has been routinely used as a reference by many universities in monitoring pesticide resistance. Third instar larvae used in bioassays were starved for 24 h prior to each study.

Plant Material

Five plant species were used as sources for natural products in this study. Whole plant extractions were made of Bifora radians Bieb. (Apiaceae), *Arctium lappa* L. (Asteraceae), and *Verbascum songaricum* (Scrophulariaceae). *B. radians* is an annual forb from Europe, now introduced into the Americas. *A. lappa*, greater burdock, is broadly distributed throughout Europe and North America. *Verbasum songaricum*, mullein, is perennial plant of Central Asia and it was introduced to America as medical herb. *Xanthium strumarium* L. (Asteraceae) (cocklebur) is a North American species introduced to India and distributed widely across and the fruits of this plant were extracted. Hops, *Humulus lupulus* (Cannabinaceae), were the fifth species extracted, using only the flower bud.

All plant material was collected during spring and summer of 2002 in Ta şli çiftlik, Tokat, a temperate region of Turkey, at 600 m above sea level and where the soil is a sandy loam. Samples were dried at room temperature for three weeks in the dark and subsequently were ground in a mill (M20 Universal Mill, IKA Group, Wilmington, N.C., USA). Ground plants were stored in 21 glass jars at 18±2° C. in the dark until extraction.

To prepare an extract, 50 g of a sample was placed into a 1 l Erlenmeyer flask with 500 ml of methanol (Sigma). Flasks were covered with aluminum foil, placed on a horizontal shaker (HS 260 Basic, IKA Group) and shaken (120 oscillations/min for 24 h) in the dark. The suspension was filtered through two layers of cheese cloth, transferred into a 250 ml evaporating flask and excess methanol was evaporated in a rotary evaporator (RV 05 Basic 113, IKA Group) at 32±2° C. The resulting residue was weighed and eluted with sufficient acetone to yield a 40% (w/w) stock plant suspension. For each species, the stock suspension was then diluted with acetone to give solutions containing 0.2%, 2% or 20% (w/w) plant suspension.

Bioassay Procedures

Leaflets were removed from healthy potato, *Solanum tuberosum* L., plants and a 2 $cm^2$ disc was cut from each using a cork borer. Potato leaflet discs were immediately dipped into one of the treatment solutions or the solvent control for 5 s. The disks were left to dry under a fume cabinet for 15 min at room temperature. Each disc was transferred into a 6 cm diameter Petri dish and a third instar Colorado potato beetle larva was placed on the disc. The dish was set 7 cm beneath a black and white CCD camera (Shebar, Burton, Mich., USA). The dish was illuminated with a dissecting lamp (Schott, Elmsford, N.Y., USA), and ambient light was minimized. The cameras were connected to a computer (Gateway, Irvine, Calif., USA) with video-input which was digitally recorded using TVR 2.0 video recording software (Homestretch, Austin, Tex., USA). Video recording commenced immediately following the placement of the insect, and each was recorded for 15 minutes. Five minute-long recordings were made every two hours for 24 hours to assess the insects' feeding activity throughout exposure to the extracts. Ten insects were used for each treatment and for the control.

Video recordings from the first 15 minutes of the observations were analyzed using The Observer 5.0 behavior analysis software (Noldus Information Technologies, Wageningen, The Netherlands). The following behavioral states were recorded; feeding, resting, and walking. From these data, the amount of gustatory interaction and leaf rejections were calculated. Resting, feeding, and walking were recorded as states and the frequency and duration of each of these behaviors was recorded. Rejection was also recorded, with this being defined as the insect leaving the leaflet and remaining away from the leaf until the end of the observation. Some insects left the leaflet and walked on the dish, but only for a short period of time, coming back eventually. These were not considered to be rejections.

After each recording, the test leaflet was dried at 40° C. in a gravity convection incubator (GCA Precision, Winchester, Va., USA) for 24 h, and was then weighed on an electronic balance (Sartorius, Goettingen, Germany) in order to assess the amount of leaf tissue ingested by each insect. Leaves treated with acetone were placed into Petri dishes for 24 h in the bioassay room and were also weighed to provide a positive control for changes in leaf weight.

Results

Leaf Consumption

Extracts of all five plant species tested had antifeedant activity against *L. decemlineata* larvae, with varying levels of consumption among the different extracts (Table 11). Reduction in leaf consumption was dependent on the concentration of extract, with consumption decreasing with increasing concentration for all extracts. No significant inhibition of leaf consumption was observed for the 0.2% extracts (F=1.32, df=5, 54, P 0.27), whereas all except the *Verbascum songaricum* extract caused significant protection against leaf consumption at 2.0% (F=25.49, df=5, 54, P<0.000). All of the extracts were highly active at the 20% concentration (F=72.02, df=5, 54, P<0.0001). The 20% *H. lupulus* and *X. strumarium* extracts caused the greatest reduction in consumption of leaflets and they were significantly different from other plant extracts.

Frequency of Feeding

The frequency with which beetles initiated feeding bouts during the first 15 minutes of exposure to the leaves was significantly affected by the different extracts when tested at 2% (F=11.29, df=5, 54, P<0.0001) and 20% (F=6.06, df=5, 54, P=0.0002) concentrations (Table 2). However, at 0.2% there was no significant effect of extract on the frequency of feeding (F=0.98, df=5, 54, P=0.47). More than 70% of beetles exhibited feeding on leaves when the extracts were tested at 0.2% concentration. When the concentration was raised to 2.0%, feeding frequency declined to between 0-30% (Table 2), depending on the plant extract tested.

Time Spent Feeding

The total time spent feeding by beetles in the first 15 minutes of exposure to the treated leaves varied significantly according to the different plant extracts when they were provided at 2.0% (F=18.69, df=5.54, P<0.0001) and 20% (F=9.31, df=5.54, P<0.0001), but not at 0.2% (F=1.77, df=5.54, NS) (Table 3). At the lowest concentrations of all extracts, beetles spent more than 70% of their time feeding, whereas once the concentration was raised to 2%, a significant reduction of feeding activity was observed for all extracts tested. The extract of *V. songaricum* showed the least reduction of feeding at 2% concentration, with extracts of *A. lappa* and *B. radians* completely suppressing feeding behavior at this concentration. At 20% concentration, feeding was suppressed completely by extracts of *A. lappa, B. radians, H. lupulus,* and *X. strumarium*.

Rejection of Treated Leaves

Figure 3:
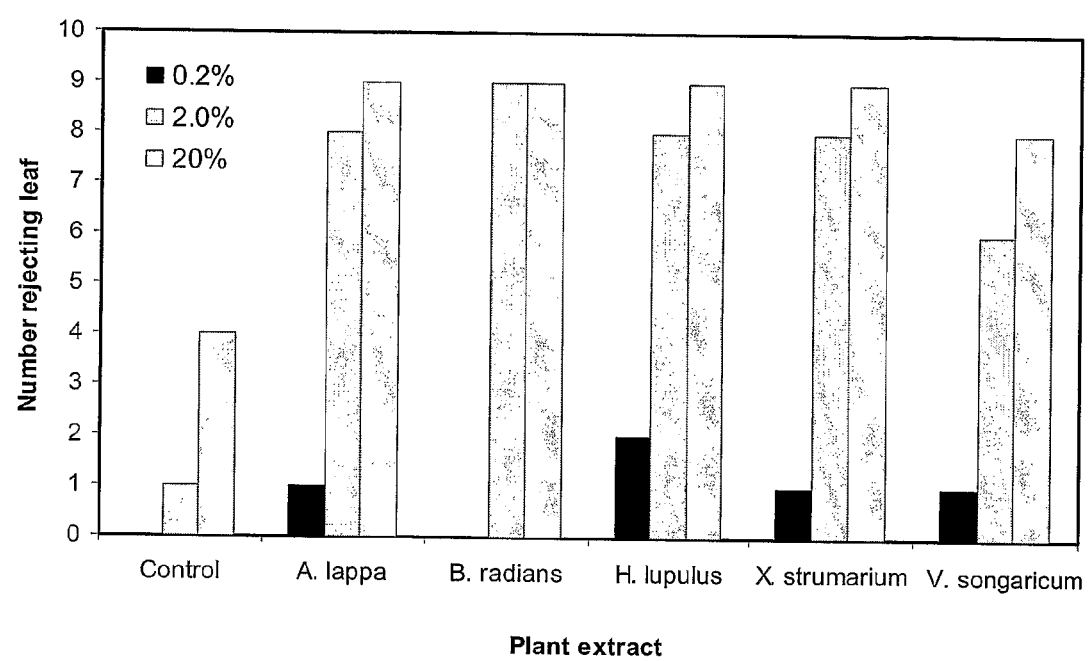
FIG. 3 shows the number of *L. decemlineata* beetles (out of ten) that rejected a potato leaf during a 10 minute observation.

No more than four of the ten larvae tested were observed to reject untreated leaves (FIG. 3). Leaves treated with the 0.2% extract solutions were also rarely rejected, whereas at the 2.0% concentrations, 6-9 of the beetles rejected the leaves and at 20% 8-9 beetles rejected the leaf. Although none of the extracts caused complete rejection of the leaf, the extract of *B. radians* caused the greatest rejection at the 2.0% concentration (FIG. 3). Average times until rejection were compared for the 2.0% concentration treatments, revealing a range in the time until beetles rejected the leaves, from 68.3±18.7 s for the *B. radians* extract to 259.9±50.9 s for the extract of *H. lupulus*. Despite this variation in rejection time, this behavior was not affected significantly by the different extracts (F=1.29, df=5.54, P=0.28).

TABLE 11

Average amount (mg) of potato leaf remaining after 24 h exposure to Colorado potato beetle larvae.

| Treatment | Plant extract concentration (% w/w) | | |
|---|---|---|---|
| | 0.2% | 2.0% | 20.0% |
| Control | 1.51 ± 0.89 a | 1.69 ± 0.69 c | 2.24 ± 0.83 c |
| *Arctium lappa* | 2.15 ± 0.61 a | 3.38 ± 0.32 b | 6.72 ± 0.63 b |
| *Bifora radians* | 1.93 ± 0.76 a | 3.75 ± 1.39 b | 7.00 ± 1.31 b |
| *Humulus lupulus* | 2.23 ± 0.59 a | 6.91 ± 0.79 a | 8.25 ± 0.67 a |
| *Verbascum songaricum* | 2.15 ± 0.55 a | 2.91 ± 0.10 bc | 6.60 ± 0.67 b |
| *Xanthium strumarium* | 2.12 ± 0.89 a | 4.20 ± 1.74 b | 8.12 ± 0.68 a |

Values in a column followed by the same letter are not significantly different (P < 0.05).

TABLE 12

Frequency of feeding by *L. decemlineata* larvae on potato leaves treated with 0.2, 2.0 and 20% (w/w) concentration solutions of plant extracts.

| Plant | Concentration (w/w) | | |
|---|---|---|---|
| | 0.2% | 2.0% | 20.0% |
| Untreated | 0.9 ± 0.1 a | 0.9 ± 0.1 a | 0.6 ± 0.2 a |
| *Arctium lappa* | 0.8 ± 0.1 a | 0.2 ± 0.1 c | 0.0 ± 0.0 b |
| *Bifora radians* | 1.0 ± 0.0 a | 0.2 ± 0.1 c | 0.0 ± 0.0 b |
| *Humulus lupulus* | 0.7 ± 0.2 a | 0.0 ± 0.0 b | 0.0 ± 0.0 b |
| *Verbascum songaricum* | 0.7 ± 0.2 a | 0.3 ± 0.2 b | 0.1 ± 0.1 b |
| *Xanthium strumarium* | 0.7 ± 0.2 a | 0.1 ± 0.1 b | 0.0 ± 0.0 b |

Values in the same column followed by the same letter are not significantly different (P < 0.05).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

TABLE 13

Average time ± S.E. (s) spent feeding by *L. decemlineata* larvae on potato leaves treated with 0.2, 2.0 and 20% (w/w) concentration solutions of plant extracts.
Values in the same column followed by the same letter are not significantly different (P < 0.05).

| Plant extract | Concentration (w/w) | | |
|---|---|---|---|
| | 0.2% | 2.0% | 20.0% |
| Untreated | 468.7 ± 54.2 a | 481.9 ± 54.6 a | 297.7 ± 85.2 a |
| *Arctium lappa* | 411.1 ± 73.2 a | 43.8 ± 42.8 b | 0.0 ± 0.0 b |
| *Bifora radians* | 529.3 ± 10.6 a | 34.1 ± 31.3 b | 0.0 ± 0.0 b |
| *Humulus lupulus* | 292.7 ± 75.8 a | 0.0 ± 0.0 b | 0.0 ± 0.0 b |
| *Verbascum songaricum* | 324.6 ± 83.1 a | 160.5 ± 81.7 b | 25.8 ± 25.8 b |
| *Xanthium strumarium* | 359.8 ± 80.2 a | 28.1 ± 8.1 b | 0.0 ± 0.0 b |

The invention claimed is:

1. A plant extract consisting essentially of an acetone and methanol extract of the flower bud of hops, wherein said plant extract exhibits biopesticide activity against *Leptinotarsa decemlineata*, and wherein said hops are from a temperate region of Turkey.

* * * * *